(12) United States Patent
Fujieda et al.

(10) Patent No.: US 11,596,922 B2
(45) Date of Patent: Mar. 7, 2023

(54) POROUS FIBER, ADSORBENT MATERIAL, AND PURIFICATION COLUMN

(71) Applicant: Toray Industries, Inc., Tokyo (JP)

(72) Inventors: Hiroaki Fujieda, Otsu (JP); Yoshiyuki Ueno, Otsu (JP); Kazumi Tanaka, Otsu (JP)

(73) Assignee: TORAY INDUSTRIES. INC., Tokyo (JP)

( * ) Notice: Subject to any disclaimer, the term of this patent is extended or adjusted under 35 U.S.C. 154(b) by 44 days.

(21) Appl. No.: 16/096,530

(22) PCT Filed: Apr. 20, 2017

(86) PCT No.: PCT/JP2017/015863
§ 371 (c)(1),
(2) Date: Oct. 25, 2018

(87) PCT Pub. No.: WO2017/188110
PCT Pub. Date: Nov. 2, 2017

(65) Prior Publication Data
US 2019/0126239 A1    May 2, 2019

(30) Foreign Application Priority Data

Apr. 27, 2016 (JP) .............. JP2016-089682

(51) Int. Cl.
*B01J 20/26* (2006.01)
*B01J 20/30* (2006.01)
(Continued)

(52) U.S. Cl.
CPC .......... *B01J 20/261* (2013.01); *A61M 1/1621* (2014.02); *A61M 1/36* (2013.01);
(Continued)

(58) Field of Classification Search
CPC .... A61M 1/1621; A61M 1/36; A61M 1/3646; A61M 1/3679; A61M 2202/0427;
(Continued)

(56) References Cited

U.S. PATENT DOCUMENTS 9,821,501 B2   11/2017   Fujimura et al.
2007/0000507 A1*   1/2007   Xue .................... D01F 9/14
                                                   131/361
(Continued)

FOREIGN PATENT DOCUMENTS

JP    58169510 A    10/1983
JP    0542207 A    2/1993
(Continued)

OTHER PUBLICATIONS

Chen, et al., "Calculation Method of Specific Surface Area of Foam Metal Based on an Ideal Tetradecahedron Model for Lithium Ion Battery," Int'l J. of Photoenergy, vol. 2020, 1-7 (Year: 2020).*
(Continued)

*Primary Examiner* — Patrick Orme
(74) *Attorney, Agent, or Firm* — RatnerPrestia

(57) ABSTRACT

A solid fiber is described, where the solid fiber is characterized by (a) a modification degree Do/Di, in a cross section of the solid fiber of 1.20 to 8.50 where the inscribed circle diameter is denoted by Di and the circumscribed circle diameter is denoted by Do; and (b) a porous specific surface area of not less than 30 m²/g.

16 Claims, 10 Drawing Sheets

(51) Int. Cl.
*B01J 20/28* (2006.01)
*D01D 5/247* (2006.01)
*D01D 5/253* (2006.01)
*A61M 1/36* (2006.01)
*B01D 15/00* (2006.01)
*B01D 15/20* (2006.01)
*A61M 1/16* (2006.01)
*B01J 20/285* (2006.01)
*D01F 6/52* (2006.01)
*D01F 6/16* (2006.01)

(52) U.S. Cl.
CPC .......... *B01D 15/00* (2013.01); *B01D 15/206* (2013.01); *B01J 20/26* (2013.01); *B01J 20/264* (2013.01); *B01J 20/28* (2013.01); *B01J 20/285* (2013.01); *B01J 20/2808* (2013.01); *B01J 20/28023* (2013.01); *B01J 20/28028* (2013.01); *B01J 20/28052* (2013.01); *B01J 20/28059* (2013.01); *B01J 20/28083* (2013.01); *B01J 20/28085* (2013.01); *B01J 20/3007* (2013.01); *B01J 20/3092* (2013.01); *D01D 5/247* (2013.01); *D01D 5/253* (2013.01); *A61M 2202/0427* (2013.01); *A61M 2202/0439* (2013.01); *B01J 2220/82* (2013.01); *D01F 6/16* (2013.01); *D01F 6/52* (2013.01); *D10B 2505/04* (2013.01); *D10B 2509/00* (2013.01)

(58) Field of Classification Search
CPC .......... A61M 2202/0439; B01D 15/00; B01D 15/206; B01J 20/26; B01J 20/261; B01J 20/262; B01J 20/264; B01J 20/28; B01J 20/28011; B01J 20/28023; B01J 20/28028; B01J 20/28052; B01J 20/28057; B01J 20/28059; B01J 20/28078; B01J 20/2808; B01J 20/28083; B01J 20/28085; B01J 20/285; B01J 20/3007; B01J 20/3092; B01J 2220/58; B01J 2220/82; D01D 5/247; D01D 5/253; D01F 6/16; D01F 6/52; D10B 2505/04; D10B 2509/00

See application file for complete search history.

(56) References Cited

U.S. PATENT DOCUMENTS

| | | |
|---|---|---|
| 2014/0364307 A1 | 12/2014 | Onohara |
| 2017/0333871 A1 | 11/2017 | Fujieda et al. |

FOREIGN PATENT DOCUMENTS

| | | |
|---|---|---|
| JP | 06296860 A | 10/1994 |
| JP | 07171360 A | 7/1995 |
| JP | 10251915 A | 9/1998 |
| JP | 1136272 A | 2/1999 |
| JP | 2009167128 A | 7/2009 |
| JP | 2010148851 A | 7/2010 |
| JP | 2010188253 A | 9/2010 |
| JP | 2011156022 A | 8/2011 |
| WO | 2011129023 A1 | 10/2011 |
| WO | 2013111857 A1 | 8/2013 |
| WO | 2016067967 A | 5/2016 |

OTHER PUBLICATIONS

International Search Report and Written Opinion for International Application No. PCT/JP2017/015863, dated Aug. 1, 2017, 7 pages.
Ishikiriyama et al., "Pore Size Distribution Measurements of Silica Gels by Means of Differential Scanning Calorimetry II. Thermoporosimetry", Journal of Colloid and Interface Science, 1995, vol. 171, pp. 103-111.
Scaler Corporation, Image Measurement Software MicroMeasure Version 1.04 (Mar. 17, 2010), Operating Manual downloaded from the internet at www.scalar.co.jp/products/micromeasure.php?page=download&cat=software, 29 pages.

* cited by examiner

[Fig. 1]
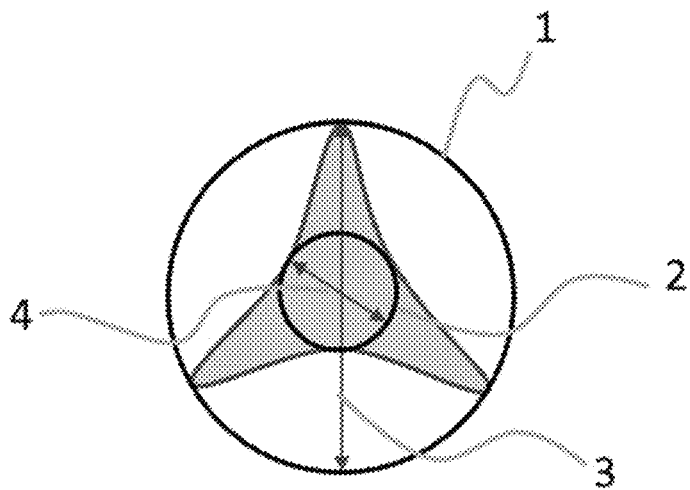
[Fig. 2]
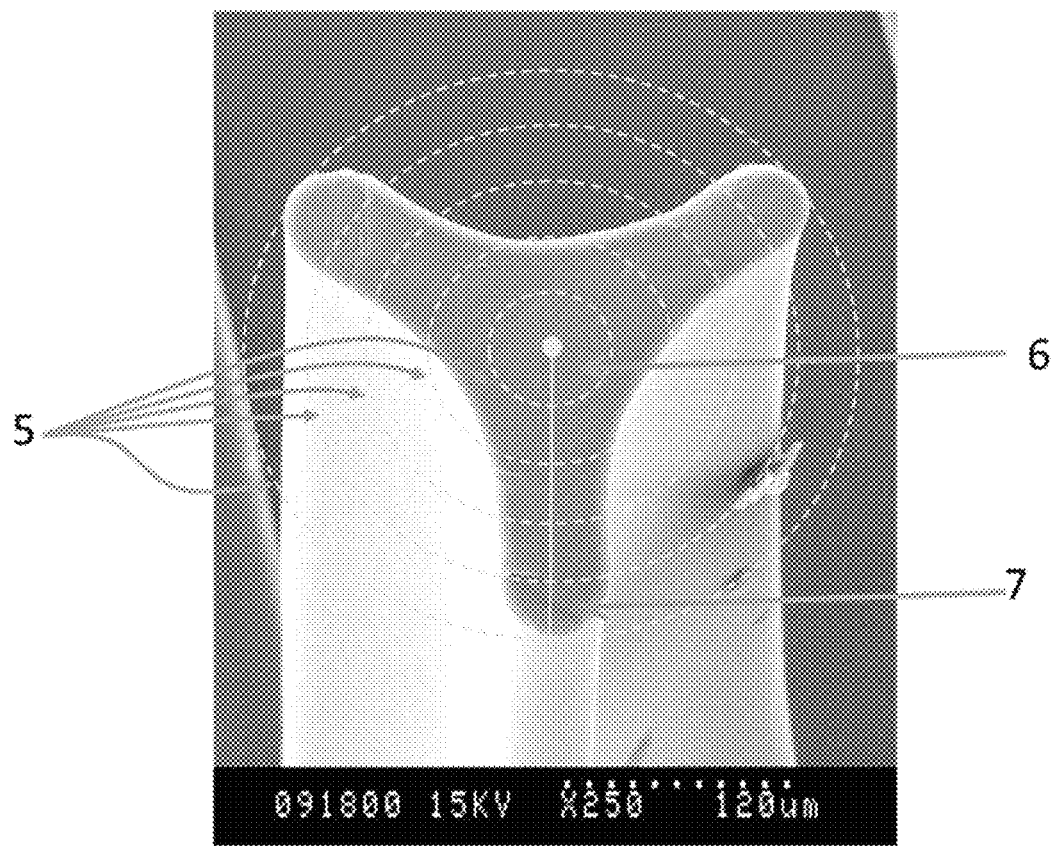

[Fig. 3]
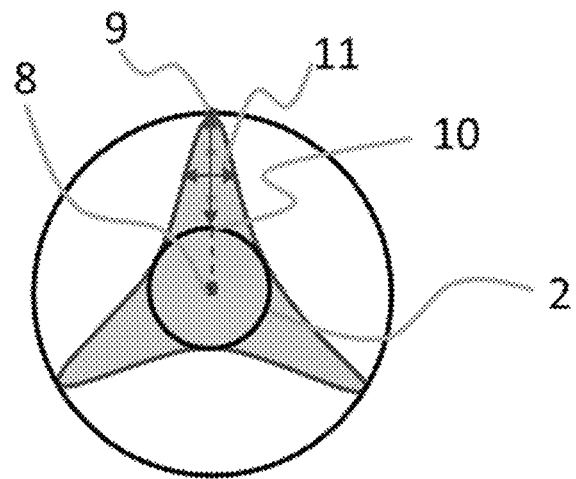
[Fig. 4]
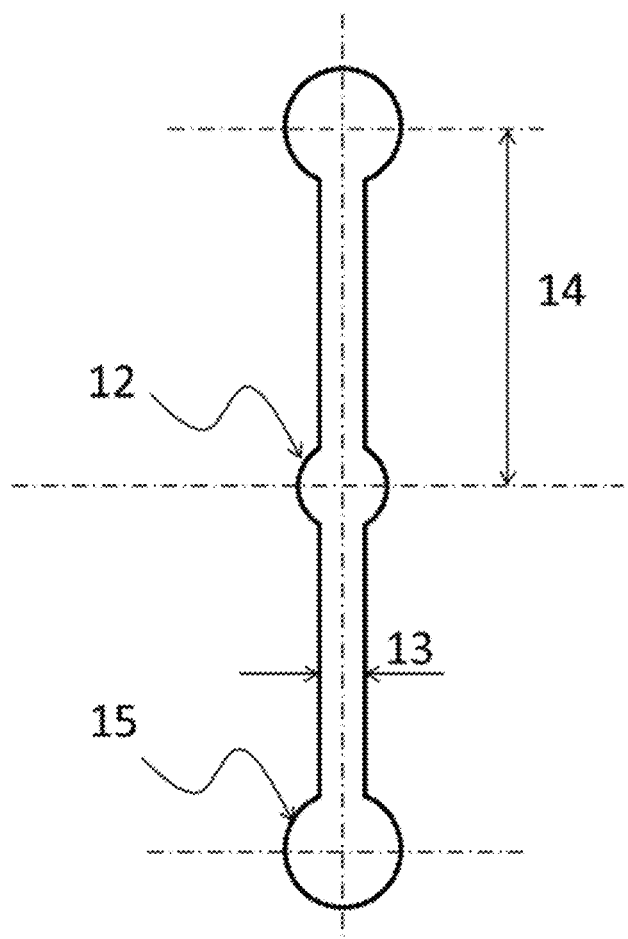

[Fig. 5]
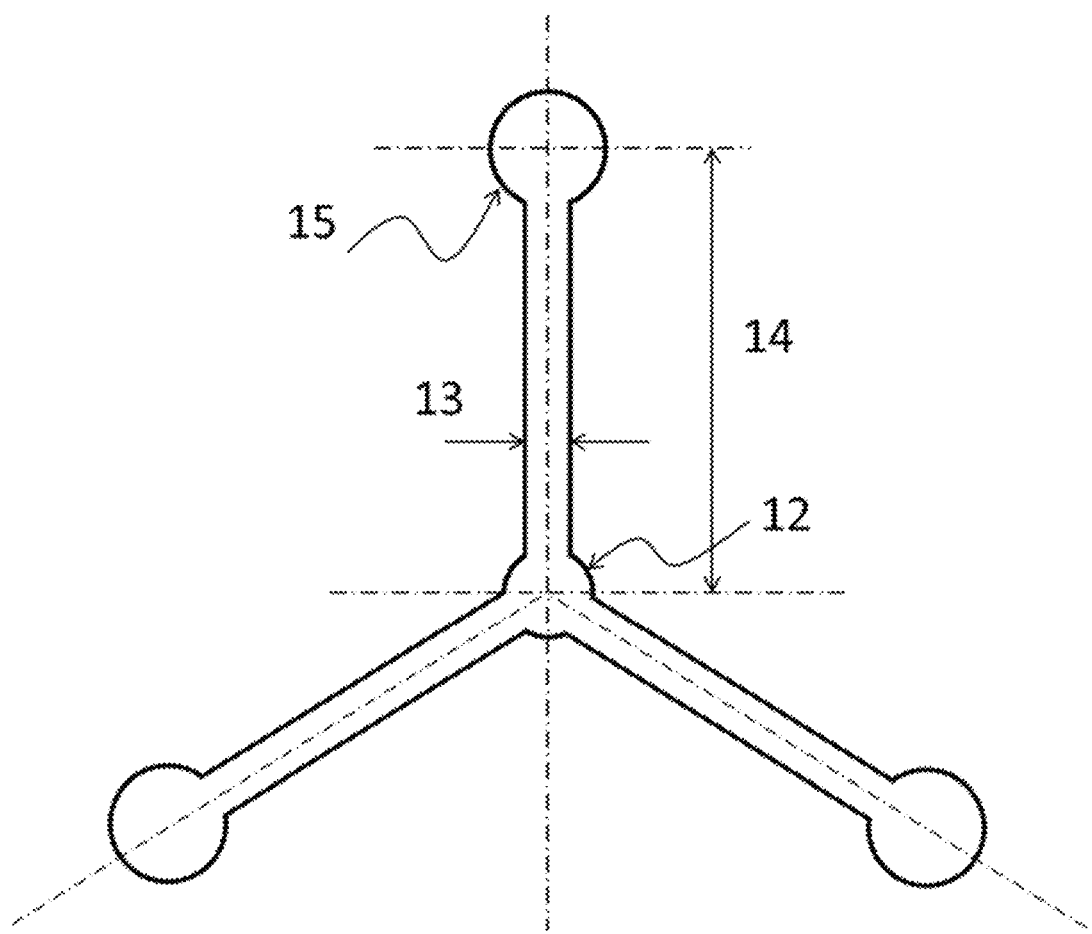

[Fig. 6]
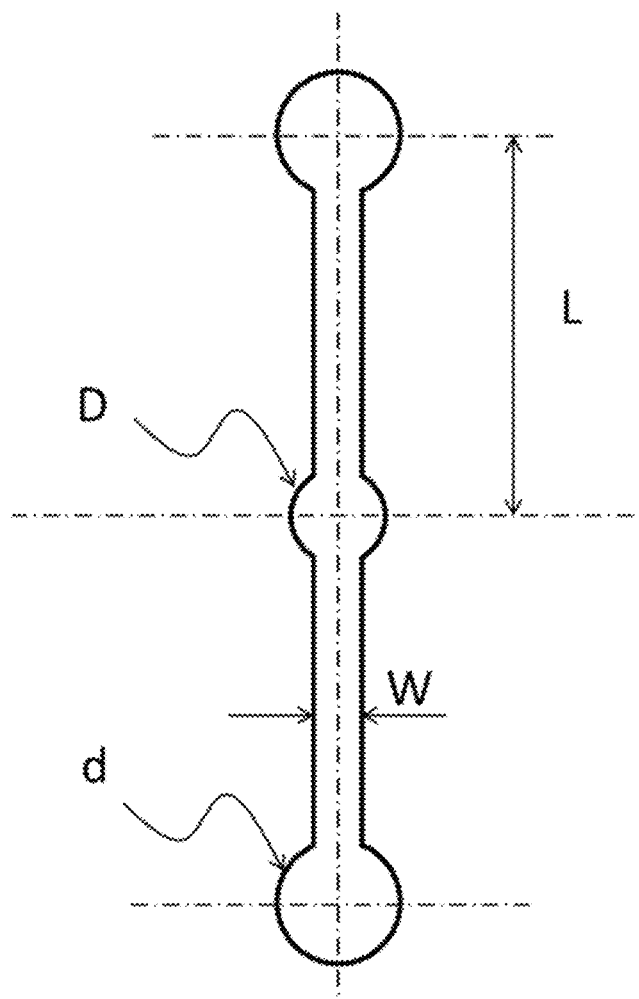

[Fig. 7]
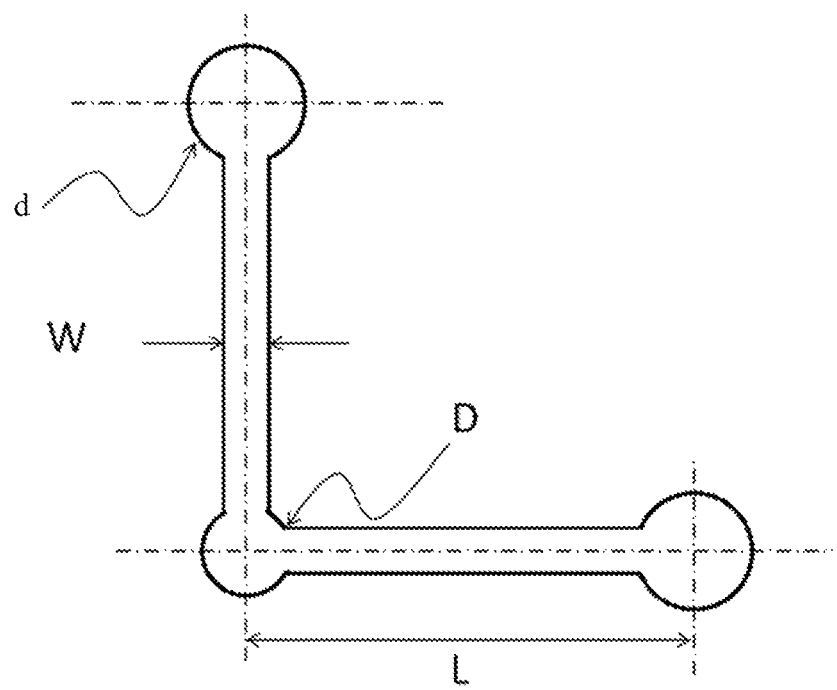

[Fig. 8]
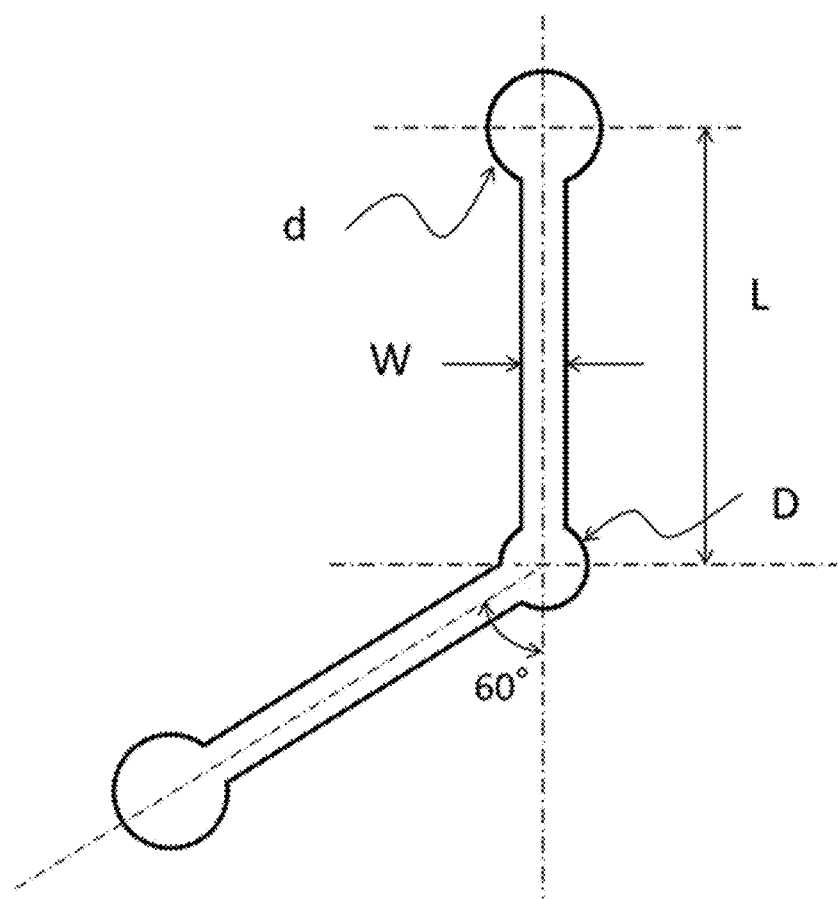

[Fig. 9]
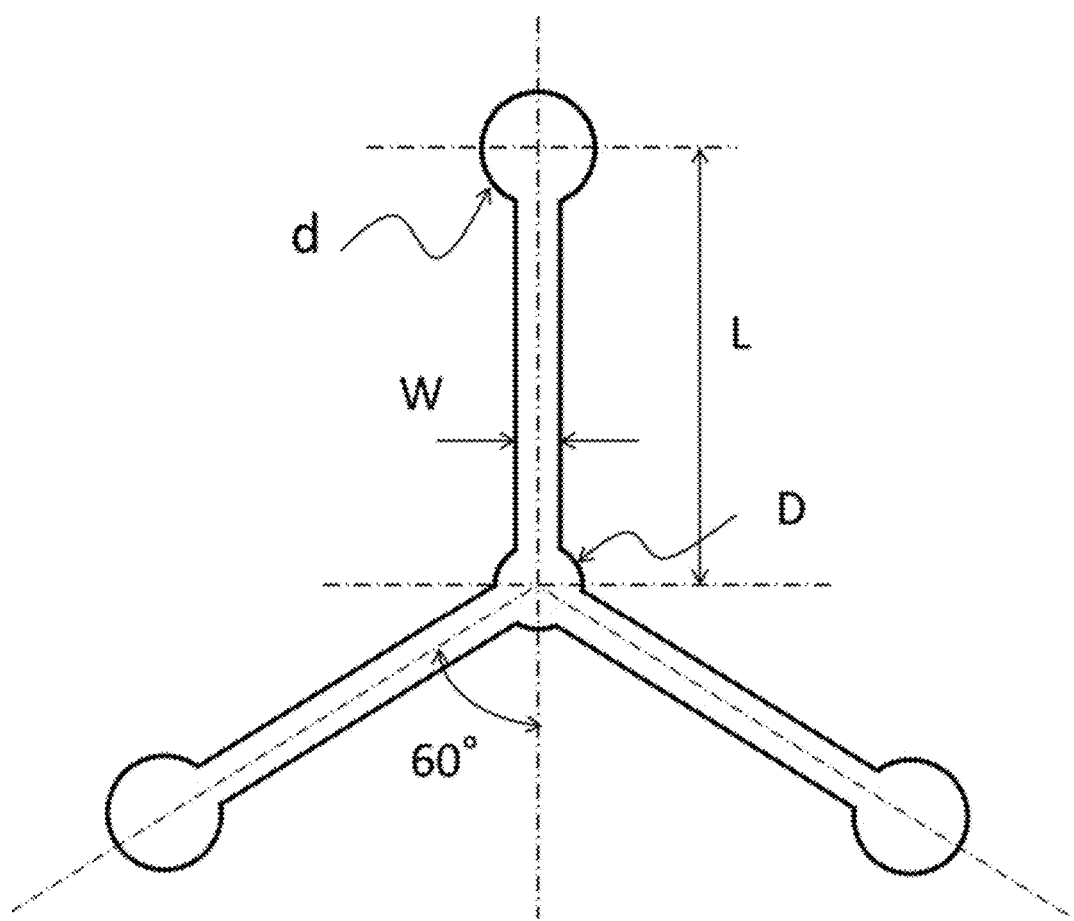

[Fig. 10]
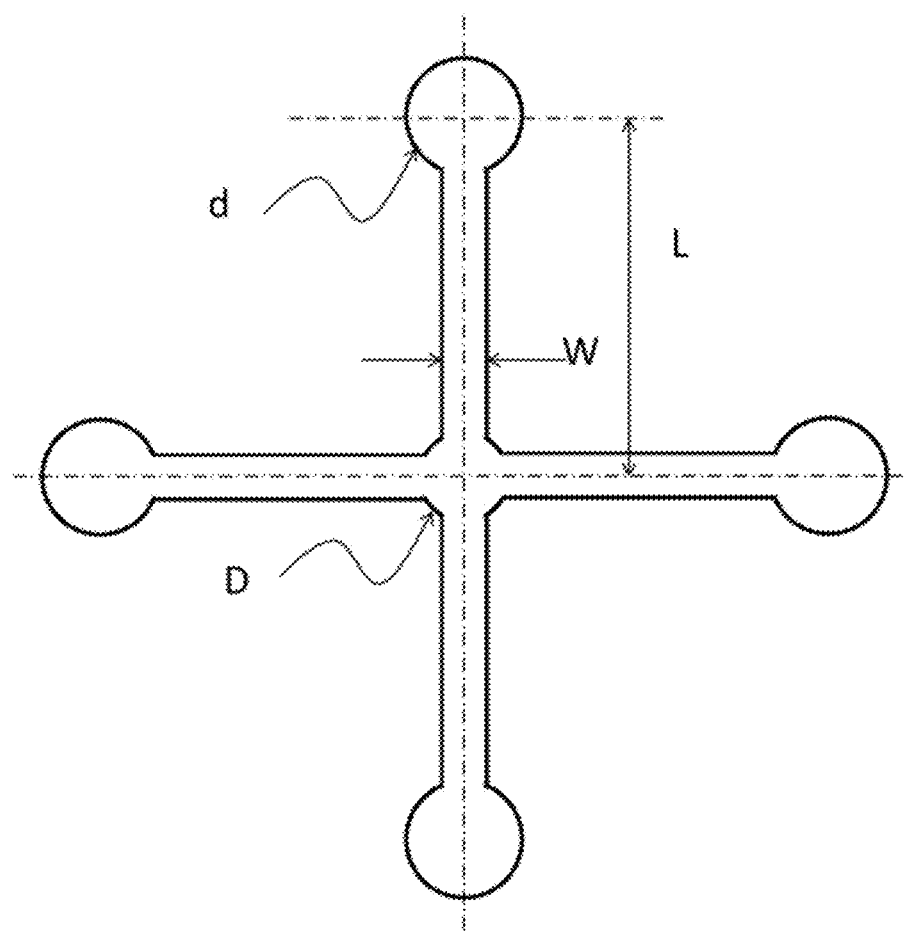

[Fig. 11]
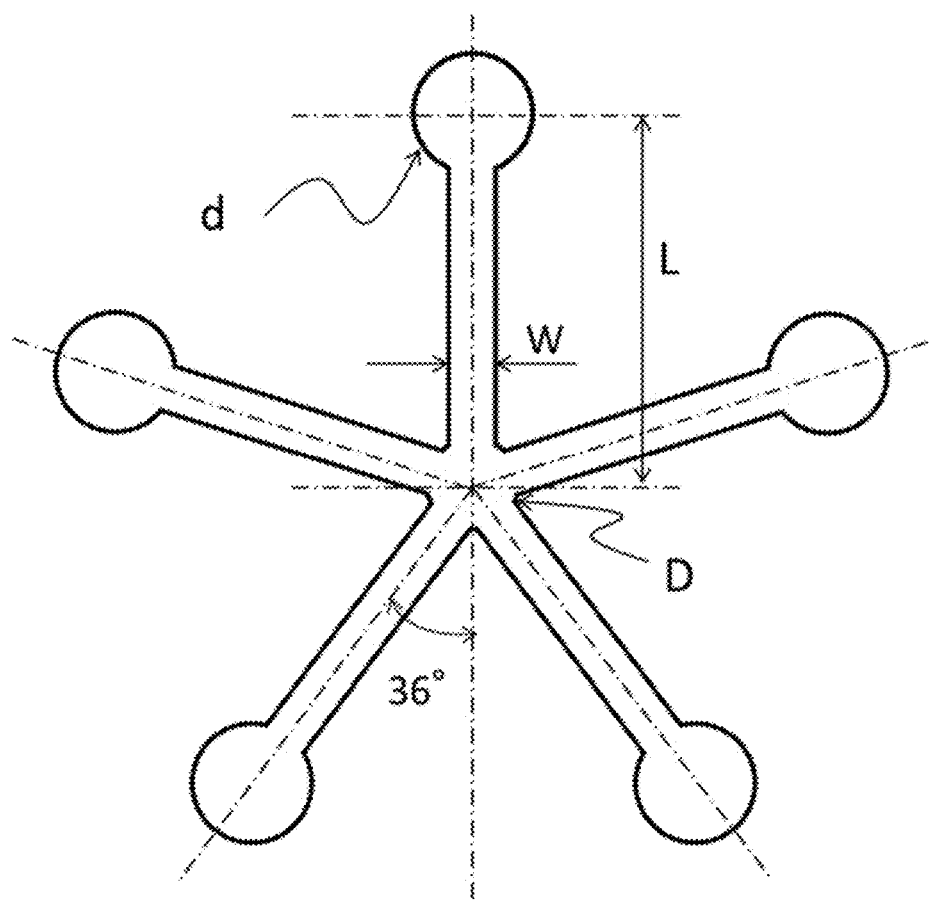

[Fig. 12]
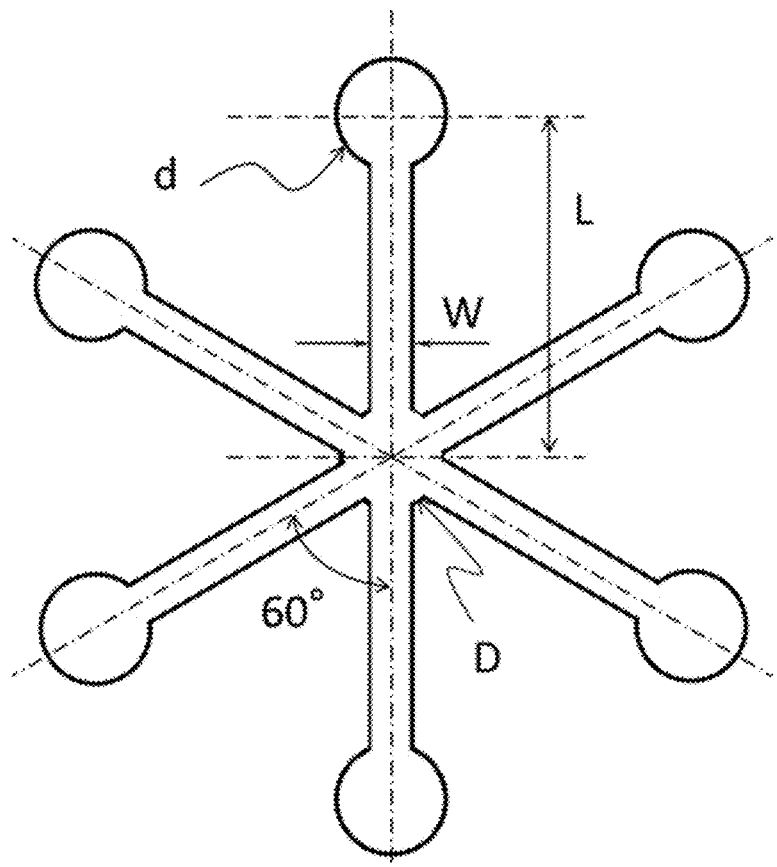
[Fig. 13]
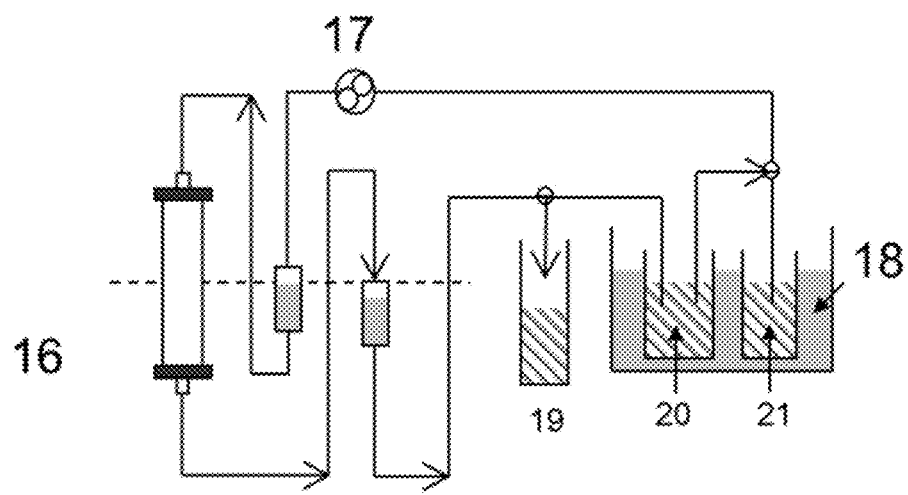

POROUS FIBER, ADSORBENT MATERIAL, AND PURIFICATION COLUMN

CROSS REFERENCE TO RELATED APPLICATIONS

This is the U.S. National Phase application of PCT/JP2017/015863, filed Apr. 20, 2017, which claims priority to Japanese Patent Application No. 2016-089682, filed Apr. 27, 2016, the disclosures of each of these applications being incorporated herein by reference in their entireties for all purposes.

FIELD OF THE INVENTION

The present invention relates to a porous fiber. Particularly, the present invention relates to a porous fiber which can efficiently adsorb a removal target substance in the fluid that is to be treated, an adsorbent material formed by using such a porous fiber as a bundle, and a purification column which incorporates the porous fiber.

BACKGROUND OF THE INVENTION

Conventionally, porous beads are often used as the form of the adsorbent material to be used for the purification column which removes, by adsorption, a removal target substance in the fluid that is to be treated. Examples of the reasons for this include the fact that bead-shaped adsorbent has advantages of less unbalanced blood flow in a column and hence ease of a column design because the adsorbent can be uniformly packed into an adsorption column. On the other hand, examples of a means for improving adsorption capacity include increasing of a surface area per volume of the adsorbent. However, when the adsorbent is bead-like, a bead diameter is decreased in order to increase a surface area per volume of the adsorbent, a gap between the beads becomes narrow. Therefore, since resistance of a flow path becomes high to increase a pressure loss, it becomes difficult to pass the fluid that is to be treated. Further, the bead used as an adsorbent is usually spherical, and therefore it has a disadvantage that the surface area per volume is inherently small. That is, even though there is an adsorption reserve capacity inside the bead, an internal adsorption site cannot be effectively used.

Examples of the form of an adsorbent material other than the bead include a fiber, it is also thought to use a fiber having a common round cross section. Examples of the form of the fiber include one obtained by inserting a large number of fibers in the straight form in parallel to a lengthwise direction of a column case, or one obtained by forming a knitting fabric.

In the knitting fabric of these forms, it is difficult in production to make the fiber porous for providing adsorption holes for the fiber. Further, when the fluid that is to be treated includes many dissolved substances and viscosity is high, it is not so preferred since processing easily results in a pressure rise in a column.

On the other hand, the fiber of the form obtained by inserting a filament fiber such as a solid fiber or a hollow fiber in the straight form in parallel to a lengthwise direction of a column case, can secure a flow path of the fluid that is to be treated separately from the adsorbent material. Therefore, the fiber of this form can suppress resistance of the flow path, and is advantageous to the adhesion of a dissolved substance in the fluid that is to be treated.

Here, a method in which a shape other than a circular shape is used as a cross-section shape of the fiber, that is, a fiber with a modified cross section is used, is known. However, it is heretofore thought that since spinning stability deteriorates when the modification degree of the fiber is increased, an increase of the modification degree has been suppressed. Particularly, in the case of the porous fibers, there has been a fear that strength-elongation of the fiber is significantly reduced and unevenness of a fiber diameter referred to as draw resonance increases by a modified cross section, and in addition to this, there has been a fear that modification of a cross-section shape, particularly, agglutination between the protrusions within a single fiber cross section, occurs.

Hitherto, the inventions concerning a purification column into which hollow fibers or solid fibers are incorporated are disclosed (Patent Documents 1 and 2).

Here, a method in which a shape other than a circular shape is used as a cross-section shape of the fiber, that is, a fiber with a modified cross section is used, is known. However, it is heretofore thought that since spinning stability deteriorates when the modification degree of the fiber is increased, an increase of the modification degree is suppressed. Particularly, in the case of the porous fibers, there has been a fear that strength-elongation of the fiber is significantly reduced and unevenness of a fiber diameter referred to as draw resonance increases by a modified cross section, and in addition to this, there has been a fear that modification of a cross-section shape, particularly, agglutination between the protrusions within a single fiber cross section, occurs. However, heretofore, Patent Documents 3 to 5 describe the invention concerning the fibers with the modified cross section in which a shape other than a circular shape is used as a cross-section shape of a porous fiber.

In Patent Document 6, a separation membrane in which a modified cross section is formed is described. In Patent Document 7, a hollow fiber in which an oval cross section is formed is also described.

On the other hand, Patent Document 8 describes the invention concerning the fibers with the modified cross section which has no hollow portion, but pores on the surface.

PATENT DOCUMENTS

Patent Document 1: Japanese Patent Application Laid-Open No. (JP-A) 2011-156022
Patent Document 2: Japanese Patent Application Laid-Open No. (JP-A) 2010-148851
Patent Document 3: Japanese Patent Application Laid-Open No. (JP-A) 58-169510
Patent Document 4: WO 2011/129023 A
Patent Document 5: Japanese Patent Application Laid-Open No. (JP-A) 2010-188253
Patent Document 6: Japanese Patent Application Laid-Open No. (JP-A) 07-171360
Patent Document 7: Japanese Patent Application Laid-Open No. (JP-A) 05-042207
Patent Document 8: Japanese Patent Application Laid-Open No. (JP-A) 10-251915

NON-PATENT DOCUMENT

Non-patent Document 1: Kazuhiko Ishikiriyama et al., JOURNAL OF COLLOID AND INTERFACE SCIENCE, (1995) Vol. 171, 103-111.

SUMMARY OF THE INVENTION

However, cross-section shapes of the fibers used in these Patent Documents 1 and 2 are round, and the adsorption capacity has been low since the surface area per volume of the adsorbent is small.

The fibers described in Patent Documents 3 to 5 are all for hollow fiber types of separation membranes. In case of hollow fibers, deformation of a cross-section shape described above hardly occurs since structural fixation can be performed at the same time from both sides of the inside of a fiber (=hollow portion) and the outside of a fiber in forming a fiber (=spinning). The structural fixation is performed by cooling with cool wind or by bringing into contact with a poor (non)solvent. Therefore, the hollow fiber is more advantageous than the solid fiber which can be cooled only from the outside of the fiber. As results of viewing each of concepts/objects of modifying a fiber shape in Patent Documents described above, prevention of intimate contact between bundles in bundling the fibers (Patent Document 3) and suppressing fouling by complicating and disturbing a flow on an outer surface of a hollow fiber ((Patent Documents 4 and 5) are mainly described. That is, shapes provided with short protrusions on the periphery of a fiber are merely employed for the object different from the present invention. Particularly, the above concept of suppressing fouling is contrary to the concept of an adsorption column which adsorbs a dissolved substance on the fiber. Accordingly, a concept of improving the adsorption capacity by increasing a surface area per volume is not present. Therefore, a shape in which the modification degree is not very high is shown. In addition, in Patent Documents 3 to 5, a thick dense layer (separation layer) is present on the surface of a fiber, and therefore, an adsorption target substance cannot reach pores within the fibers and thereby resulting in deterioration of the adsorption capacity. Further, in such fibers, since it is assumed to use the fibers for separation application, a specific surface area of pores is small. In addition, since the fibers have an asymmetric structure in a film thickness direction, a pore radius distribution is wide.

However, with respect to its "separation" function, a paragraph [0005] in the specification describes "one of performance indexes as a multilayer composite separation membrane is a permeation rate, and when a membrane material is the same, it is important to decrease a thickness of a separation layer and to increase a membrane area of a separation layer so as to enhance a permeation rate. That is, it is assumed that a target substance is separated by passing across a membrane. From such a viewpoint, a cross-section shape is modified with the intention of improving separation performance by increasing a membrane area of a separation membrane. Accordingly, specifically, a hollow fiber membrane is described, thus, and a fiber with a solid form is not substantially described. In Patent Document 6, pore opening is performed by stretching of a modified cross-section fiber prepared by melt spinning. Accordingly, it is difficult to control a porous specific surface area by forming a network structure by having many pores. Its microcrack structure is elongated in stretching to form pores having various sizes, and the porous specific surface area is therefore reduced. Further, since a pore radius distribution tends to be wider, a pore having a much smaller pore radius than that of the material to be adsorbed cannot contribute to the adsorption. That is, an area, not contributing to the adsorption, of the porous specific surface area is partially present. Further, since pore opening is performed by stretching of the fiber, a support material of the fiber is limited to a crystalline polymer. Likely, Patent Document 7 does not describe a solid fiber and the intent of forming an oval cross-section is not clear.

That is, a technology of modifying a cross-section shape of a hollow fiber which is used in the above document is not a technology designed in consideration of use of a fiber as an adsorbent material.

In the invention described in Patent Document 8, pores are used for dividing a fiber so as to increase a fiber volume and are hence small. That is, the pore is largely different in pore radius, pore radius distribution and porous specific surface area from the pore for adsorption, and it is hard to say that the fiber is a material generally referred to as a porous fiber.

An object of the present invention is to provide a porous fiber having excellent removal performance with respect to a material to be adsorbed, and a purification column which incorporates an adsorbent material obtained by bundling the fibers.

In order to solve the above-mentioned problem, the porous fiber according to one aspect of the present invention comprises the following constitution. That is:

A porous fiber comprising a modified solid cross-section, wherein the porous fiber satisfies the following (a) to (b):

(a) a modification degree Do/Di, in a cross section of the solid fiber, is 1.20 to 8.50 when the inscribed circle diameter is denoted by Di and the circumscribed circle diameter is denoted by Do; and (b) a porous specific surface area of the fiber is not less than 30 m$^2$/g.

The adsorbent material according to one aspect of the present invention has the following constitution. That is:

An adsorbent material, comprising not less than 28 vol % of the above-mentioned porous fiber as a fiber bundle.

The purification column according to one aspect of the present invention has the following constitution. That is:

A purification column which is formed by arranging the above-mentioned adsorbent material in the straight form in an axis direction of a plastic casing and by attaching an inlet port and an outlet port of a fluid that is to be treated to both ends of the plastic casing.

The porous fiber according to the present invention preferably has an average radius of pore of not less than 0.8 nm and not more than 90 nm.

The porous fiber according to the present invention preferably has a porous specific surface area of not less than 30 m$^2$/g.

The porous fiber according to the present invention preferably has an inscribed circle occupancy, which is represented as the following equation, of not less than 0.10.

Inscribed circle occupancy=Area of the inscribed circle of the cross section of the fiber/Area of the cross section of the fiber.

The porous fiber according to the present invention preferably has a diameter of pore not more than 25 μm and a ratio of an average diameter of pore in the area adjacent to the outer surface of the fiber vs an average diameter of pore in the central portion area of the fiber is preferably not less than 0.50 and not more than 3.00.

The porous fiber according to one aspect of the present invention has a structure of fiber cross-section comprising a porous portion which has a network structure composed of a communication hole and a dense layer which has a more dense structure in comparison to the porous portion, and wherein the porous fiber preferably satisfies the following (d) to (e):

(d) the porous portion and the dense layer are continued with each other; and (e) the dense layer is located closer to the area adjacent to the outer surface of the fiber than the porous portion and a distance T1 from the most outer surface of the fiber to the porous portion is not less than 0.001 µm and not more than 30 µm.

In the porous fiber according to the present invention, when a circle equivalent diameter (µm) is denoted by T2, T1 and T2 preferably satisfy the following equation:

$$T1/T2 \geq 0.030.$$

In the porous fiber according to the present invention, the solid fiber is preferably in a straight form.

In the porous fiber according to the present invention, a circle equivalent diameter T2 is preferably not less than 10 µm and not more than 1,000 µm.

In the porous fiber according to the present invention, an open pore ratio at surface is preferably not less than 0.5% and not more than 30%.

In the porous fiber according to the present invention, a pore radius distribution index is preferably not less than 1.0 and not more than 2.8.

In the porous fiber according to the present invention, both the porous portion and the dense layer preferably contain 45 vol % or more of a material common to both as a component material.

The porous fiber according to the present invention preferably has a negative charge.

The porous fiber according to the present invention preferably comprises an amorphous polymer material.

Preferably, the porous fiber according to the present invention comprises an amorphous polymer material and the amorphous polymer material comprises a polymer with an ester group.

In the porous fiber according to the present invention, the number of adhered platelets which are brought into contact with the surface of the porous fiber is preferably not more than $30/(4.3 \times 10^3 \mu m^2)$.

The porous fiber according to the present invention is preferably for use in a medical application.

In the porous fiber according to the present invention, an adsorption amount of $\beta_2$-microglobulin per fiber volume is preferably not less than 0.005 mg/cm³.

According to the present invention, it is possible to provide a porous fiber which can efficiently adsorb a removal target substance in the fluid that is to be treated, and a purification column which incorporates the porous fiber.

BRIEF DESCRIPTION OF THE DRAWINGS

FIG. 1 is a fiber cross-sectional view for explaining an inscribed circle and a circumscribed circle.

FIG. 2 is a fiber cross-section photograph showing a central portion area and an area adjacent to the outer surface of the cross section.

FIG. 3 is a view for explaining a protrusion thickness ω.

FIG. 4 is a view of a spinneret for producing a fiber having protrusion number of 2, and a view for explaining each part of the spinneret.

FIG. 5 is a view of a spinneret for producing a fiber having protrusion number of 3, and a view for explaining each part of the spinneret.

FIG. 6 is a view of a spinneret for producing a fiber having protrusion number of 2 (an oval shape).

FIG. 7 is a view of a spinneret for producing a fiber having protrusion number of 2 (an L-shape).

FIG. 8 is a view of a spinneret for producing a fiber having protrusion number of 2 (a V-shape with obtuse angle).

FIG. 9 is a view of a spinneret for producing a fiber having protrusion number of 3.

FIG. 10 is a view of a spinneret for producing a fiber having protrusion number of 4.

FIG. 11 is a view of a spinneret for producing a fiber having protrusion number of 5.

FIG. 12 is a view of a spinneret for producing a fiber having protrusion number of 6.

FIG. 13 is a circuit diagram at the time of measuring adsorption capacity of a column.

DETAILED DESCRIPTION OF EMBODIMENTS OF THE INVENTION

The porous fiber according to the present invention is referred to as a solid fiber and has a configuration/form of a porous fiber having no hollow portion. In case of a hollow fiber, even if an outer surface of the hollow fiber is formed into a fiber having a modified cross section and the fluid that is to be treated is brought into contact with only the outside of the hollow fiber, a surface area inside the hollow fiber cannot be effectively used. Further, when the fluid that is to be treated is passed through inside the hollow fiber, the effect of the modified cross section cannot be achieved. Although there is a technique in which the fluid that is to be treated is passed through both inside and outside of the hollow fiber, it is difficult to equally distribute the flow into inside and outside, and uneven flow tends to occur. For example, an operation in which, after blood is flowed as a fluid that is to be treated, the blood remaining in the column is returned to the body using saline (sometimes referred to as "blood reinfusion"), is conducted. Especially in case of a small inner diameter of the hollow fiber, this operation is not preferred since there is a fear of the occurrence of a phenomenon referred to as residual blood in which a large amount of blood remains within the hollow fiber during blood reinfusion.

Further, a plurality of monofilaments of a solid fiber may be entangled to form a multi-filament, but this is not preferred since a tangled portion hardly comes into contact with the fluid that is to be treated, so that there is a high possibility that the surface area cannot be effectively used for adsorption. Note that the multi-filament as used herein means a yarn composed of a large number of monofilaments. The multi-filament includes both of one composed of the same fibers and one composed of different types of fibers.

The porous fiber in the present invention has a modified cross-section shape, whereby the surface area per volume is increased, and it can be consequently expected that the adsorption capacity is improved. The modified cross-section shape of the porous fiber can be represented by modification degree. The modification degree referred to herein is a value represented by a ratio between an inscribed circle diameter and a circumscribed circle diameter in observing the fiber cross section, that is, a ratio Do/Di between the inscribed circle diameter Di and the circumscribed circle diameter Do.

Here, the modified cross section may have a shape retaining symmetry such as line symmetry and point symmetry or may have an asymmetric shape. When it is determined that the modified cross section retains mostly line symmetry and/or point symmetry, the inscribed circle is a largest circle inscribed in a curve which forms the outline of a fiber in the fiber cross section, and the circumscribed circle is a circle circumscribing a curve which forms the outline of a fiber in the fiber cross section. In FIG. 1, a circumscribed circle, an inscribed circle, and diameters Do and Di of a fiber which has a Y-shaped cross section are shown as one example of a fiber with a modified cross section.

On the other hand, when it is determined that the modified cross section does not retain line symmetry or point symmetry at all, the inscribed circle and the circumscribed circle are defined as follows. The inscribed circle is to be a circle having the maximum radius which circle is possible within the range in which the circle inscribes a curve which forms the outline of a fiber at least at two points, the circle is present only inside the fiber and the circumference of the inscribed circle does not intersect with the curve which forms the outline of the fiber. The circumscribed circle is to be a circle having the minimum radius which circle is possible within the range in which the circle circumscribes a curve which forms the outline of a fiber at least at two points, the circle is present only outside the fiber and the circumference of the circumscribed circle does not intersect with the outline of the fiber.

When the modification degree is less than 1.20, the capacity of the fiber to adsorb a removal target substance is insufficient. The reason for this is that the surface area per volume is generally decreased as the modification degree is decreased, and therefore the adsorption capacity is reduced. The lower limit of modification degree is preferably not less than 1.50, more preferably not less than 1.80, and still more preferably not less than 2.00. On the other hand, it is necessary to set a certain upper limit for the modification degree, and the upper limit is set to not more than 8.50, in the present invention, preferably not more than 6.50, and more preferably not more than 4.00. When the modification degree exceeds 8.50, the cross section shape is elongated, and therefore, the cross section shape cannot be maintained due to decrease of strength and elongation of the fiber, and bending of protrusions, ablating protrusions and the like tend to occur in case that the fiber has protrusions which are present in the outer periphery of the fiber cross section. Furthermore, the spinning stability may be decreased and it may be hardly to maintain the fiber shape. When the spinning solution previous to forming a fiber is quickly cooled with use of a gas or liquid, the above-mentioned protrusions interferes with the wind or liquid flow. As a result of this, there is concern that unevenness generates even in a microstructure such as a fiber shape and the pore/surface opening.

Examples of the fiber cross section shapes having protrusions include an oval shape, an L-shape and a V-shape with obtuse angle when the shape has two protrusions. They include a Y-shape and T-shape when the shape has three protrusions. They include a cross shape when the shape has four protrusions and star shape when the shape has five protrusions. The upper limit of the protrusion number is preferably not more than 12, more preferably not more than 8, still more preferably not more than 6, and particularly preferably not more than 4. When the spinning solution is quickly cooled with use of a gas or liquid, an extremely rough portion of the fiber can be cooled evenly and structural unevenness hardly occurs as long as the protrusion number is within this preferred range. Furthermore, the adsorption capacity can be enhanced since the fluid that is to be treated can easily enter among the protrusions.

As a method of measuring the modification degree, both ends of a fiber to be measured are fixed while applying tension of 0.1 g/mm$^2$ to the fiber and cut the fiber at a random position. Thereafter, a cut surface is enlarged with an optical microscope, DIGITAL MICROSCOPE DG-2 manufactured by Scalar Corporation, and a photograph is taken. In taking a photograph, a photograph of a scale is also taken at the same magnification. After the image is digitized, the circumscribed circle diameter Do and the inscribed circle diameter Di of the cross section of the fiber are measured using an image analysis software "Micro Measure ver. 1.04" manufactured by Scalar Corporation. Then, the modification degree of each fiber is determined from the following formula. This measurement is carried out for 30 positions, and measured values are averaged and a value obtained by rounding off the average value to two decimal places is defined as a modification degree.

Modification degree=$Do/Di$.

The porous fiber according to the present invention has pores inside the porous fiber. The lower limit of the average radius of the pores inside the porous fiber is preferably not less than 0.8 nm, more preferably not less than 1.5 nm, and particularly preferably not less than 2.0 nm. On the other hand, the upper limit of the average radius of the pores is preferably not more than 90 nm, more preferably not more than 55 nm, and particularly preferably not more than 30 nm. When the average radius of the pores is within the above-mentioned preferred range, adsorption efficiency is enhanced since a substance to be adsorbed is not only adsorbed on the fiber surface, but also enters into a pore. On the other hand, because the average radius of the pores is large to such an extent that a substance to be adsorbed in a pore space, adsorption efficiency may not be reduced.

In the porous fibers according to the present invention, the adsorption capacity can be improved by increasing a porous specific surface area of the porous fiber in order to adsorb the substance to be adsorbed. For this, the lower limit of the porous specific surface area of the porous fiber according to the present invention is not less than 3 m$^2$/g. When the porous specific surface area is less than 3 m$^2$/g, the adsorption capacity is insufficient. The porous specific surface area is preferably not less than 15 m$^2$/g, more preferably not less than 30 m$^2$/g, still more preferably not less than 60 m$^2$/g, particularly preferably not less than 170 m$^2$/g. On the other hand, the upper limit of the porous specific surface area is preferably not more than 1,000 m$^2$/g, more preferably not more than 800 m$^2$/g, still more preferably not more than 650 m$^2$/g, and particularly preferably not more than 500 m$^2$/g. When the porous specific surface area is within the above-mentioned preferred range, the mechanical strength may not be insufficient.

The average radius of the pores of the porous fibers and porous specific surface area can be determined by measuring a freezing point depression due to capillary condensation of water in a pore by differential scanning calorimetry (DSC) using a differential scanning calorimeter (DSC). The measurement method is as described in Non-patent Document 1. That is, the melting point of ice confined in a nanosized pore is lower compared to normal bulk ice (melting point: 0° C.). Utilizing this phenomenon, Laplace equation and Gibbs-Duhem equation can be combined based on a distribution of the melting point from the DSC curve, and then the pore radius distribution can be calculated to obtain the average pore radius.

Specifically, a melting point lowering degree $\Delta T$ is larger as pore radius R is smaller, and $\Delta T$ and R are represented by the following equation. Where $\alpha$ is a constant (nmK) as a function of temperature, is 56.36$\Delta T$−0.90 for freezing process, and 33.30ΔT−0.32 for melting process. The first item α/ΔT of the equation represents a diameter of freezable water in a pore. The second item β represents a thickness of non-freezable water adsorbing on a pore surface.

Further, a DSC curve profile reflects a pore distribution curve of a porous body, and the pore distribution curve (dV/dR) can be calculated from the DSC curve (dq/dt). Furthermore, a porous specific surface area can be determined by the following equation.

$$\text{Porous Specific Surface Area} = \int \frac{Z}{R}\left(\frac{dV}{dR}\right) dR \qquad \text{[Math 1]}$$

where V: cumulative pore volume, m: weight of a porous body (solid fiber), ΔH(T): melting enthalpy at a temperature T, p(T): density of pore water at a temperature T, Z: pore shape factor (cylinder 2.0, sphere 3.0).

After removing water adhered to a surface of the solid fiber sample which was dipped in water, the resulting sample is provided as approximately 5-mm-long fibers, and tens of them are packed in a sealed pan, weighed and subjected to measuring by DSC. The sample is cooled to −55° C. and then measured while heating at a temperature rising rate of 0.3° C./min. DSC Q100 manufactured by TA Instruments, Inc., is used as a DSC instrument.

In the porous fibers according to the present invention, a cross section of the fiber may be a heterogeneous structure or may be a homogeneous structure. Particularly, the fiber having a homogeneous structure is preferred since it has a homogeneous porous structure in a cross sectional direction of the fiber and therefore more adsorption area can be secured.

However, the porous fiber may have a slightly gradient structure such that pores in a periphery of the fiber are enlarged and a size of pores is gradually reduced toward a fiber center portion in order to reduce diffusion resistance to the fiber center portion. Further, in such a condition that pores on the outermost surface of the fiber are completely blocked due to fouling over time, a risk that pores even inside the fiber is blocked is reduced by having such a gradient structure. Consequently, it is possible to suppress a phenomenon in which diffusion of the material to be adsorbed to the fiber center portion deteriorates. In such a homogeneous structure, a ratio of an average diameter of pores in the area adjacent to the outer surface of the fiber to an average diameter of pores in the central portion area of the fiber (average diameter of pores in the area adjacent to the outer surface/average diameter of pores in the central portion area) is preferably not less than 0.50 and not more than 3.00, more preferably not less than 0.75 and not more than 2.00, and still more preferably not less than 0.85 and not more than 1.50.

Further, a heterogeneous structure having macrovoids or the like as often observed for fibers prepared by a nonsolvent induced phase separation process is not preferred since it reduces a surface area per volume and deteriorates physical properties of the fiber. The macrovoid as used herein refers to a spherical and/or oval pore having a diameter of 25 μm or more. The diameter as used herein refers to a minor axis of the pore in case that a shape of the pore is other than a sphere, for example, an egg shape. That is, in the porous fiber according to the present invention, the diameter of a pore in the porous fiber is preferably not more than 25 μm. In other words, it is preferable that the porous fiber according to the present invention have no pore of which a substantial diameter exceeds 25 μm. In the present invention, a method of determining whether a macrovoid of the fiber is present is as follows. First, the porous fiber is cut in a cross sectional direction of the fiber to allow a cross section to be exposed, and the cross section is used as an observation sample. A photograph of this cross section is taken using DIGITAL MICROSCOPE DG-2 manufactured by Scalar Corporation or the like to determine whether a pore of which a diameter exceeds 25 μm is present. This procedure is repeated for arbitrary 50 cross sections, and the fiber is regarded as having macrovoids when 10 or more cross sections among the above 50 cross sections are determined to have a pore of which a diameter exceeds 25 μm.

Next, a method of determining a homogeneous structure in the present invention will be described.

First, the porous fibers are adequately moistened, and then immersed in liquid nitrogen to freeze water content inside pores momentarily with liquid nitrogen. Thereafter, the fiber is quickly folded, frozen water content is removed in a state that a fiber cross section is exposed in a vacuum dryer at 0.1 torr or less to obtain a dry sample. Thereafter, a thin film of platinum (Pt), platinum-palladium (Pt—Pd) or the like is formed on the sample surface by sputtering to obtain an observation sample. The cross section of the sample is observed using a scanning electron microscope (S-5500, manufactured by Hitachi High-Technologies Corp.). Here, a radius passing through a center point 8 of a fiber cross section is arbitrarily selected, and then, as shown in FIG. 2, concentric circles 5 (FIG. 2) passing through points which divides a line segment of this radius into five equal length are drawn, and an area including the center point is defined as a central portion area 6 and a side which is the closest to the periphery is defined as an area adjacent to the outer surface 7. A circle equivalent diameter which is present in each of the central portion area and the area adjacent to the outer surface is determined to obtain an average diameter of pores in each portion area. In calculating the average diameter of pores in each portion area, using a scanning electron microscope (magnification: 50,000 times), areas of 2 μm×2 μm of 20 locations are arbitrarily selected and photographs of them are taken, and a pore of which whole body is included in the photograph taken is measured and an average diameter of pores is calculated. In measurement of a diameter of pores, a transparent sheet is overlaid on a printed electron microscope image, and a portion corresponding to a pore is filled with black using a black marker. Thereafter, by copying the transparent sheet on a white paper, a black pore area is clearly distinguished from a white non-pore area, and a diameter of pores is determined using an image analysis software.

Further, a pore radius distribution index of the porous fiber is preferably not less than 1.0 and not more than 2.8, and the upper limit thereof is more preferably not more than 2.4, and still more preferably not more than 1.9. The reason for this is that it is possible to impart size selectivity of the substance to be adsorbed by making a pore radius distribution uniform as possible.

The pore radius distribution index is determined by a method which utilizes DSC as average radius of pores, and a value obtained by dividing a secondary average pore diameter by a primary average pore diameter is taken as a pore radius distribution index. Detailed measurement and calculation methods are described in Non-patent Document 1.

Moreover, the porous fiber that may be used for the present invention preferably has a three-dimensional network structure. The three-dimensional network structure as used herein refers to a structure in which an index of pore shape Dxy is controlled.

Index of pore shape in a cross section in the fiber axis direction $Dxy$=(pore diameter in the lengthwise direction of the fiber)/(pore diameter in the cross-section direction of the fiber)

The lower limit of Dxy is preferably not less than 0.2, more preferably not less than 0.4, and still more preferably not less than 0.6. The upper limit of Dxy is preferably not more than 6.0, more preferably not more than 4.0, and still more preferably not more than 2.5. A fiber produced by a stretch-opening method or the like has a characteristic oriented structure in the longitudinal direction of the fiber, so that it generally has a structure in which Dxy is very high, which cannot be said to be desirable.

A method of measuring Dxy is described below. A double-faced tape was bonded to a plastic plate such as polystyrene and a fiber to be measured is fixed thereon. The bonded fiber is shaved in the lengthwise direction using a single-edged cutter to expose a cross section in the lengthwise direction of the fiber, and this is bonded to a sample stage of a scanning electron microscope with a double-faced tape. It requires careful attention since exact images cannot be obtained if pores are crushed due to this shaving. Thereafter, a thin film of platinum (Pt) or Pt—Pd is formed on the surface of the fiber by sputtering to obtain an observation sample. A cross section in the lengthwise direction of the fiber is observed at a magnification of 50,000 times using a field emission-typed scanning electron microscope (S-5500, manufactured by Hitachi High-Technologies Corp.) and the images of 10 points arbitrarily selected are captured in a computer. A size of images to be captured is preferably 640 pixel×480 pixel. From one image thus obtained, 5 pores are arbitrarily extracted, and a pore diameter in the lengthwise direction of the fiber, a pore diameter in the direction of the fiber axis and a ratio between both pore sizes are determined. This procedure is carried out for the above-mentioned images of 10 points to determine the above ratio for total 50 pores, an average of these ratios is calculated, and a value obtained by rounding off the average value to one decimal place is defined as Dxy.

The cross section of the porous fiber according to the present invention is of a shape which has a porous portion having a network structure composed of a communication hole in the center part of the cross section and a dense layer having a more dense structure in comparison to the porous portion in an area adjacent to the periphery of the fiber. The porous portion and the dense layer preferably have a continuous structure. When the porous portion and the dense layer are continuous, the dense layer is hardly peeled, and therefore there is no concern that mechanical strength of the fiber is reduced and that a particulate generates.

In a cross section of the fiber, in order to obtain a continuous structure of a porous portion and a dense layer of the fiber, the porous portion and the dense layer both comprise a common material in an amount of not less than 45 vol %, more preferably not less than 85 vol %, and particularly preferably 100 vol %. When a solvent is used as a spinning solution for the porous portion and the dense layer, the same solvent is preferably used.

The continuous structure of the porous portion and the dense layer in the present invention refers to a structure in which a discontinuous change such as a gap between the porous portion and the dense layer cannot be observed in observing a cross section of the fiber by the same procedure as the method of determining a homogeneous structure described above.

In addition, in order to obtain sufficient adsorption capacity, it is important to control a thickness of the dense layer which is present in an area adjacent to the surface of the porous fiber. When the thickness of the dense layer is suitable, a material to be adsorbed can be effectively diffused to the pores inside the fiber in addition to adsorption on the fiber surface, and thereby resulting in enhancement of the adsorption capacity.

When a distance from the outermost surface of the fiber to the porous portion is a thickness of the dense layer T1, T1 is preferably not more than 30 μm, more preferably not more than 8.0 μm, still more preferably not more than 3.0 μm, and particularly preferably not more than 1.6 μm. Further, when the dense layer is not present, that is, in case of the fiber in which an internal three-dimensional network structure is exposed to outside, the three-dimensional network structure is dynamically brittle, so that there is a possibility that it could be damaged by application of an external physical force. As a result, there is also a possibility that the adsorption capacity is reduced and/or that fine particles generated due to damages, or the like flow out of the column. On the other hand, it is preferred, from the viewpoint of stably maintaining the modified cross section shape, that T1 be not less than 0.001 μm. Because the quantity of the dense layer per cross section can be increased by modification of a cross section of a fiber according to the present invention, the strength can be enhanced even when T1 is equal in comparison with such a round fiber that a modification degree Do/Di is less than 1.20.

In order to measure a thickness of the dense layer T1, a fiber cross section obtained by the same procedure as the observation sample prepared in determining the homogeneous structure described above is used. A cross section of the fiber is observed at a magnification of 30,000 times using a scanning electron microscope (S-5500, manufactured by Hitachi High-Technologies Corp.), and an image is captured in a computer. A size of an image to be captured is preferably 640 pixel×480 pixel. Next, the sample is observed using SEM to measure diameters of pores which can be identified in a fiber cross section. Here, when a pore in the cross section is blocked, preparation of a sample is made again. Note that blocking of a pore may occur by deformation of a fiber due to application of stress during cutting the porous fiber. A SEM image is cut out in the form of a rectangular body having a length of 6 μm in a direction parallel to the surface of the porous fiber and an arbitrary length in a direction perpendicular to the surface of the porous fiber, and the image is subjected to image analysis using an image processing software. The length in a direction perpendicular to the surface is required to be a length within which the dense layer falls. A threshold level is determined so that a structure portion constituting a fiber is bright luminance and the other portion is dark luminance by binarization and an image in which a bright luminance portion is white and a dark luminance portion is black is obtained. When the structure portion cannot be separated from the other portion since a difference in contrast in the image is small, the image is divided to each part in which a range of contrast is equal, each part is subjected to binarization and then combined with each other as it was before and reproduced to one image. Otherwise, image analysis may be carried out by filling an area other than the structure portion with black. An image reproduces a cross section from an outermost layer to a back layer, and therefore, there may be a case that a pore is doubly observed in a depth direction, and in this case, a pore on a shallow side is measured. When a part of a pore is present out of an image area of measurement object, the pore is excluded. The number of pixels of a scale bar indicating a known length in the image is measured, and a length per pixel is calculated. The number of pixels of a pore is measured, and a pore area is determined by multiplying the number of pixels of a pore by a square of the length per pixel. A diameter of a round corresponding to a pore area is calculated according to the following formula, and this is taken as a diameter of pores. Considering a circular constant to be "3.14", when pore diameter is 10 nm, a pore area is 78.5 ($nm^2$).

$$\text{Pore diameter}=(\text{pore area/circular constant})^{1/2} \times 2$$

The pore having a pore diameter of not less than 10 nm is identified, a layer in which the pore is not present is considered as a dense layer, and the shortest distance from pores having a pore diameter of not less than 10 nm to the fiber surface is considered as a thickness of the dense layer. That is, among pores having a diameter of not less than 10 nm, 5 pores found in an order of closer to the fiber surface is picked up, a vertical line is drawn to a plane into contact with each fiber surface, and each distance on the vertical line between the fiber surface and the pore having a diameter of not less than 10 nm is then determined. The same measurement is carried out for 10 sheets of images, and a value obtained by rounding off the average value of total 50 measured data to two decimal place is defined as a thickness of dense layer adjacent to the surface of the fiber.

For a method of controlling the thickness of the dense layer adjacent to the surface of the fiber, it is important to control a structure of a fiber surface in a dry zone in spinning. In order to fix a structure (solidify) of a flowable spinning solution to form a fiber shape, the raw solution may be brought into contact with a poor (non) solvent or cooled. The dry zone refers to a zone in which the spinning solution is discharged from the spinneret and flows idle until it comes into contact with the poor solvent or until it is completely structurally fixed by cooling. When the spinning solution is structurally fixed, the spinning solution adjacent to the surface is in a state in which an energy level is high. Therefore, it is thought that a support component such as a polymer is coagulated in coming into contact with a poor solvent or a moisture contained in the air, and thereby forming a fiber surface. Therefore, a porous structure needs to be determined to some extent before the spinning solution comes into contact with the poor solvent, namely, in a dry zone. Specifically, it is important to quickly induce phase separation after discharging the raw solution to adequately grow and enlarge a pore structure before coming into contact with the poor solvent, and to cool the fiber in the dry zone to increase viscosity of the raw solution and thereby suppressing coagulation due to a reduction of mobility of a support component. In order to realize this, it is important to take an adequate retention time in the dry zone. Accordingly, the retention time is not less than 0.05 second, preferably not less than 0.20 second, and more preferably not less than 0.40 second. The retention time is calculated by the following formula.

$$\text{Retention time (sec)}=\text{dry part length (m)/taken-up speed (m/sec)}$$

The open pore area of the fiber surface can be increased by reducing a surface dense layer thickness. An open pore ratio at surface of the porous fiber is preferably not less than 0.5%, more preferably not less than 1.5%, and particularly preferably not less than 2.0%. It is preferred that the open pore ratio be high in order that the substance to be adsorbed in the fluid that is to be treated is easily diffused to an adsorbing site inside the fiber. On the other hand, the upper limit of the open pore ratio is preferably not more than 30%, more preferably not more than 16%, and particularly preferably not more than 12%. When the upper limit of the porosity is within the above preferred range, a reduction of fiber strength or an increase of surface roughness does not occur. Further, it does not occur that fine particles produced inside a pore easily flow out of the fiber.

In a method of measuring an open pore ratio at surface, the fiber surface obtained by the same method as the observation sample prepared in determination of the homogeneous structure described above are observed at a magnification of 50,000 times using a scanning electron microscope (S-5500, manufactured by Hitachi High-Technologies Corp.) and the image is captured in a computer. The size of an image to be captured is preferably 640 pixel×480 pixel. An area of 6 μm×6 μm of SEM image is cut out at an arbitrary position and subjected to image analysis by an image processing software. A threshold level is determined so that a structure portion is bright luminance and the other portion is dark luminance by binarization and an image in which a bright luminance portion is white and a dark luminance portion is black is obtained. When the structure portion cannot be separated from the other portion since a difference in contrast in the image is small, the image is divided to each part in which a range of contrast is equal, each part is subjected to binarization and then combined with each other as it was before and reproduced to one image. Otherwise, image analysis may be carried out by filling an area other than the structure portion with black. A dark luminance portion in which noises are included in the image and the number of continuous pixels is five or less is considered as a bright luminance portion as a structure since the noise cannot be distinguished from the pore. In a method of eliminating noise, the dark luminance portion in which the number of continuous pixels is five or less is excluded in counting the number of pixels. Otherwise, noise portion may be filled with white. The number of pixels in the dark luminance portion is counted, and a percentage with respect to the total number of pixels in an analyzing image is calculated and the percentage is defined as an open pore ratio. The same measurement is carried out for 30 images, and an average is calculated.

In the present invention, the fiber is excellent in tensile strength at break because a thickness of the dense layer per fiber cross section area is increased by modification as described above. The fiber can be elastically deformed due to having sufficient tensile strength at break and easily maintains the physical property due to elastic deformation against stress to the fiber during a long-term storage or the like. Therefore, the tensile strength at break of the fiber is preferably not less than 560 $gf/mm^2$, more preferably not less than 900 $gf/mm^2$, and particularly preferably not less than 1,400 $gf/mm^2$.

A tensile strength at break refers to a value which is measured using TENSILON Universal Testing Machine, e.g., RTM-100 (ORIENTEC CORPORATION). Specifically, one porous fiber is gripped at the chuck of the testing machine so that the fiber length is 5 cm, and subjected to elongation at a speed of 50 mm/min in this state to measure a load (gf) at break of the fiber. This measurement is carried out ten times, and a value ($gf/mm^2$) obtained by dividing the average of data from the measurement by the fiber cross section area is considered as the tensile strength at break according to the present invention.

The tensile strength at break is important for spinning yarns continuously. When a fiber runs on driving rolls for spinning, yarn breakage can be prevented due to sufficient elongation of the fiber even in case that the fiber is elongated due to speed difference of the rolls or the like. Therefore, a tensile elongation at break is preferably not less than 10%, more preferably not less than 15%, still more preferably not less than 20%, and particularly preferably not less than 25%.

A tensile elongation at break also refers to a value which is measured using TENSILON Universal Testing Machine. Specifically, one porous fiber is gripped at the chuck of the testing machine so that the fiber length is 50 mm, and subjected to elongation at a speed of 50 mm/min in this state to measure an elongation (%) at break of the fiber. This measurement is carried out ten times, and the average of the elongation values is considered as the tensile elongation at break (%) according to the present invention.

The tensile elongation at break tends to decrease in a modified cross-section fiber. The cross section area of a fiber is reduced due to thinning by elongation, and a break occurs shortly when the cross section area is reached to a cross section area such that the fiber is intolerable to elongation. This is because a modified cross-section fiber reaches earlier to a cross section area such that the fiber is broken in thinning in comparison with a round cross-section fiber having the same cross section area. Therefore, the area of the maximum circle inscribed in a fiber cross section, namely, the area of an inscribed circle is important for a modified cross-section fiber, and this inscribed circle area is a main support area against elongation. Therefore, an inscribed circle occupancy which is represented by the following equation is preferably large.

Inscribed circle occupancy=Area of the inscribed circle/Area of the fiber cross section The lower limit of the inscribed circle occupancy is preferably not less than 0.10, more preferably not less than 0.20, still more preferably not less than 0.30, and particularly preferably not less than 0.50.

When a circle equivalent diameter of a fiber cross section is defined as T2, the upper limit of T2 is preferably not more than 1,000 μm, more preferably not more than 800 μm, and particularly preferably not more than 280 μm. When the upper limit of T2 is within the above-mentioned preferred range, the efficiency in cooling a discharged fiber is good, the modification degree as designed is maintained due to easy retaining of the fiber shape, and the fiber enters a coagulating bath including a poor solvent after sufficient cooling. Therefore, a support material such as a polymer adjacent to the surface is hardly coagulated and/or deposited and the thickness of dense layer adjacent to the surface is hardly increased, and therefore reduction of the open pore ratio at surface may not occur.

On the other hand, the lower limit of T2 is preferably not less than 10 μm, more preferably not less than 30 μm, and particularly preferably not less than 50 μm. When the lower limit of T2 is within the above-mentioned preferred range, the strength of the fiber during production processes is maintained, spinning stability and productivity are excellent, whereby a produced fiber may not be brittle. Further, an adsorption site may not be easily saturated since a volume per surface area is suitable.

In a method of measuring the above-mentioned T2, both ends of a fiber to be measured are fixed with a tension of 0.01 to 0.10 g/mm², and cut. Thereafter, a cut surface is enlarged with an optical microscope, and its photograph is taken. In so doing, a photograph of a scale is also taken at the same magnification. After the image is digitized, using an image analysis software "Micro Measure ver. 1.04" supplied by Scalar Corporation, a periphery of the cross section of the fiber is traced to calculate a cross-section area S, and a circle equivalent diameter of each opening is calculated by the following formula. An average of 30 measured data is calculated and rounded to unit.

Circle equivalent diameter of fiber cross section
$$T2=2\times(S/\pi)^{1/2}$$

The upper limit of T1/T2 is preferably not more than 0.030, more preferably not more than 0.020, and particularly preferably not more than 0.010. When the upper limit of T1/T2 is within the above-mentioned preferred range, porous portion which is an adsorption site is not relatively decreased and the adsorption site is hardly saturated, whereby the adsorption efficiency of the fiber may not be reduced.

A component material for the porous fiber in the present invention is not particularly limited, but organic substances are suitably used from the viewpoint of ease of forming process and cost, and polymethyl methacrylate (hereinafter, referred to as PMMA), polyacrylonitrile (hereinafter, referred to as PAN), polysulfone, polyether sulfone, polyaryl ether sulfone, polypropylene, polystyrene, polycarbonate, polylactic acid, polyethylene terephthalate, cellulose, cellulose triacetate, ethylene-vinyl alcohol copolymer, polycaprolactam and/or the like are used. Among these, an amorphous polymer is preferably used from the viewpoint of forming processability and cost. The porous fiber preferably comprises a material which is hydrophobic to some extent and has a property capable of adsorbing protein and the like, and examples of the materials include PMMA, PAN and the like. Especially, PMMA is preferably used since it is a representative of a fiber having a uniform structure in a thickness direction and a homogeneous structure and a structure in which a pore radius distribution is sharp are easily obtained. Further, a polymer containing an ester group is preferred since it has excellent biocompatibility and it is easy to express a function by controlling a terminal group. Particularly, PMMA is preferred since it is an amorphous polymer and has high transparency and therefore observation of an internal state of the fiber is relatively easy to evaluate a perfusion state of the fluid that is to be treated, such as a fouling.

Further, the porous fiber may have a negative charge. It is also reported that hydrophilic property is increased by containing a functional group having a negative charge in at least a part of the material, and the material tends to be finely dispersed (that is, many fine pores are formed). Examples of the functional groups having a negative charge include a sulfo group, carboxyl group, phosphate group, phosphorous group, ester group, sulfite group, hyposulphite group, sulfide group, phenolic group, hydroxysilyl group. Among these, at least one selected from a sulfo group, a carboxyl group, and an ester group is preferred. Examples of compounds having a sulfo group include vinylsulfonic acid, acryl sulfonic acid, methacrylsulfonic acid, p-styrenesulfonic acid, 3-methacryloxypropanesulfonic acid, 3-acryloxypropanesulfonic acid, 2-acrylamide-2-methylpropanesulfonic acid, and sodium salt, potassium salt, ammonium salt, pyridine salt, quinoline salt, tetramethylammonium salt thereof. An amount of a negative charge is preferably not less than 5 μeq and not more than 30 μeq per 1 g of dried fiber. The amount of negative charge can be measured using, for example, a titration method.

In addition, in order to enhance adsorbability and selectability of a substance to be adsorbed by utilizing a charge, the surface of the porous fiber may be modified. The modification refers to fixation of an anionic and/or cationic hydrophilic polymer to the surface. A method of modification is not particularly limited, but, for example, a modified fiber in which a hydrophilic polymer is fixed on the surface thereof by irradiating in a state in which the porous fiber is in contact with a solution containing a polymer can be obtained. For example, in case that a purification column is used for an application such as a medical equipment, irradiation can also serve as sterilization at the same time. Examples of the anionic hydrophilic polymer include dextran sulfate, polyvinyl sulfate, and example of the cationic hydrophilic polymer include polyalkyleneimines.

In case that the porous fiber according to the present invention is used by bringing into contact with blood components or the like for use in medical application, the fiber is preferably excellent in biocompatibility. "Excellent in biocompatibility", more specifically, means that it is preferred that the number of adhered platelets be small when human blood is brought into contact with the surface of the fiber. This is because platelets are activated by adhesion of platelets to the fiber, whereby inflammatory reaction is elicited by releasing platelet activating factor or the like. The porous fiber according to the present invention is possible to secure biocompatibility to some extent by selecting a material excellent in biocompatibility as its component material. Examples of "materials excellent in biocompatibility" as used herein include PMMA, PAN, polysulfone, polyaryl ether sulfone, cellulose triacetate, ethylene-vinyl alcohol copolymer. However, the fiber made of even these materials may easily reduce its biocompatibility if the chemical composition is changed. Especially, it has to be careful because, in the porous fiber according to the present invention, platelets are more easily adhered geometrically in comparison with a round fiber due to its modified cross-section. The detailed mechanism is not clear as the reason for this, but, examples of the reasons include a case in which the fiber has more even surfaces in an oval-shaped fiber in comparison with a round-shaped fiber, and a case in which the fiber has a crevice portion or the like in case of an L-shaped yarn, and it is considered that blood is easily pooled in such-shaped place, and thereby easy adhesion of platelets.

As a factor which causes a change in chemical composition of the fiber, a radical which generates during a long-term storage and/or by sterilization operation or the like is a major cause. A radical causes an oxidation-reduction reaction with another atom and/or molecule rapidly when it generates because of its high reactivity, resulting in a chemical change. Therefore, in order to maintain biocompatibility of a material, it is important to prevent generation of a radical as possible. A method of preventing generation of a radical effectively is to allow the fiber to be in contact with an antioxidant.

An antioxidant is required to take account of its safety, and it is required that its toxicity is low, its molecular weight is small and the like. An antioxidant refers to a molecule which has electron-donating property to another molecule and is a substance which has a property to suppress the reaction when the polymer is initiated to be radically reacted by irradiation. Examples of the general antioxidants include water-soluble vitamins such as vitamin C, polyphenols, alcohols, sugars, sodium hydrosulfite, sodium pyrosulfite, and sodium dithionate. An antioxidant is preferably brought into contact with the fiber as an aqueous solution thereof from the viewpoint of cleaning efficiency and safety in medical setting. Especially among these, an alcohol is preferred since even a small amount of alcohol is effective and it is also low in toxicity.

It is preferred that an antioxidant be allowed to be in contact with a blood contacting surface. For example, when an alcohol solution is used as an antioxidant, the alcohol concentration is preferably not less than 0.02% by weight, preferably less than 10.0% by weight, and more preferably not more than 0.20% by weight, so as to express the effect of the present invention. When the alcohol concentration is within the above-mentioned preferred range, the concentration is suitable and the effect of an antioxidant is sufficient, and decomposition due to more amount of alcohol than required amount cannot occur in a packed liquid.

In order to give an antioxidant to the fiber in spinning, the fiber may pass on-line through a bath containing an antioxidant or an antioxidant may be given off-line to the fiber. An antioxidant may be mixed with a packed liquid in a column after making the column. Especially, since a radical generates easily during sterilization, it is desirable that the sterilization be carried out in presence of an antioxidant.

In the present invention, biocompatibility can be evaluated by "the number of adhered platelets when it is brought into contact with human blood". A method of measuring it is as follows. The fiber is washed with saline. After blood is sampled from a healthy adult, heparin sodium injection (manufactured by AY Pharmaceuticals Co., Ltd.) is immediately added as an anticoagulant agent so that it is 100 U/mL. Said blood is brought into contact with the fiber within 30 minutes after sampling the blood, and shaken at 37° C. for 2 hours. Thereafter, the fiber is washed with saline, blood components are fixed with 2.5 vol % glutaraldehyde (manufactured by Nacalai Tesque Inc.) saline solution, followed by washing with distilled water. Said fiber is pasted on a sample stage for a microscope and dried under reduced pressure at 0.1 torr or less at room temperature for 10 hours. Subsequently, a platinum/palladium thin layer is formed by sputtering on a surface of a hollow fiber membrane, this is used as a sample, and the sample surface which is an inner surface of the hollow fiber membrane is observed at a magnification of 1,500 times using a field emission-typed scanning electron microscope (S-800, manufactured by Hitachi High-Technologies Corp.), and the number of adhered platelets in one visual field ($4.3 \times 10^3$ μm$^2$) is counted. This is repeated for 50 portions of the fiber surface, and the average is considered as a number of adhered platelet in contact with human blood.

The above-mentioned number of adhered platelet in contact with human blood is preferably not more than $30/(4.3 \times 10^3$ μm$^2)$, more preferably not more than $20/(4.3 \times 10^3$ μm$^2)$, still more preferably not more than $15/(4.3 \times 10^3$ μm$^2)$, and particularly preferably not more than $9/(4.3 \times 10^3$ μm$^2)$.

When the fiber is sterilized, irradiation sterilization, distillation sterilization, EOG sterilization and the like are preferably used. Among these, irradiation sterilization is often used from the viewpoint of low residual toxicity and simpleness. As radiation used, alpha ray, beta ray, gamma ray, X-ray, ultraviolet ray, electron beam and the like are used. Among these, gamma ray and electron beam are preferably used from the viewpoint of low residual toxicity and simpleness. Sterilization effect is lower as an exposure dose of radiation is lower, on the other hand, when an exposure dose of radiation is high, a polymer containing a hydrophilic group and a membrane material are decomposed, and therefore blood-compatibility may be lowered. Therefore, the exposure dose is preferably not less than 15 kGy and not more than 100 kGy.

In production of the porous fiber according to the present invention, viscosity of a spinning solution is important for preparation of the porous fiber. The lower limit of viscosity of the raw solution is preferably not less than 10 poise, more preferably not less than 90 poise, still more preferably not less than 400 poise, and particularly preferably not less than 800 poise. When the lower limit of viscosity of the raw solution is within the above-mentioned preferred range, it is easy to maintain a target shape due to a suitable flowability of the raw solution. On the other hand, the upper limit of viscosity of the raw solution at a temperature of the spinning spinneret part is not more than 100,000 poise, and more preferably not more than 50,000 poise. When the upper limit of viscosity of the raw solution is within the above-mentioned preferred range, pressure loss is not increased in discharging the raw solution and discharging stability is maintained, and furthermore it is easy to mix the raw solution.

Viscosity measurement is performed by a falling ball method in a thermostatic chamber set to a spinning temperature according to JIS Z 8803: 2011. Specifically, a viscosity tube with an inner diameter of 40 mm is filled with a spinning solution, a steel ball (material: SUS 316) with a diameter of 2 mm is dropped into the raw solution, and a time required for the ball to fall by 50 mm is measured to determine a viscosity. A temperature for measurement is set to 92° C.

In order to produce the porous fiber according to the present invention, it is important to control a shape of a discharge opening of the spinning spinneret besides the composition of a spinning solution and the contrivance at the dry part. Particularly, the porous fiber according to the present invention has a very high modification degree. That is, as shown in FIG. 4 to FIG. 12, the shape of the discharge opening of the spinning spinneret preferably has a central circle portion 12, a slit portion 13 and a tip circle portion 15. Further, it is preferred to appropriately design a central circle diameter D, a width of the slit portion W, a length of the slit portion L and a tip circle diameter d. When such a preferred shaped spinneret is used, a draft at the dry part is not too large because a cross section area of the discharge opening is suitable, fiber diameters as referred to as draw resonance and an uneven modification degree hardly occur, and spinning is easily carried out.

The slit portion is important in determining the modification degree, and the modification degree can be improved by increasing a value L/W obtained by dividing its L by W. Therefore, the lower limit of L/W is preferably not less than 1.9, more preferably not less than 2.8, still more preferably not less than 5.5, and particularly preferably not less than 9.5. On the other hand, the upper limit of L/W is not more than 50, and particularly preferably not more than 20. The upper limit of L/W is within the above-mentioned preferred range, a protrusion shape of the fiber is not elongated too much, a spinning is stable, and an agglutination between protrusions within a single yarn hardly occurs.

The tip circle diameter d is preferably larger than a certain value in forming a shape of a modified cross section, and the protrusion width can be controlled by changing d. That is, the protrusion shape index ω/Di which is a ratio between a protrusion width ω and an inscribed circle diameter of a fiber cross section Di can be increased as d is increased. The upper limit of d is not more than 1.0 mm, more preferably not more than 0.6 mm. The upper limit of d is within the above-mentioned preferred range, the protrusion width ω and the protrusion shape index ω/Di is not too large, the tip portion does not thicken, or the cross section shape is not caused to be deformed (agglutination between protrusions within a single fiber) due to poorly cooling at the dry part.

The lower limit of W is not less than 0.005 mm, more preferably not less than 0.010 mm. The lower limit of W is within the above-mentioned preferred range, pressure loss is not increased in a spinneret or it is hard to be affected by Barus effect. On the other hand, the upper limit of W is not more than 1.00 mm, more preferably not more than 0.50 mm, and still more preferably not more than 0.25 mm. When the upper limit of W is within the above-mentioned preferred range, because a cross section area of the discharge opening is suitable, a draft at the dry part is not increased too much, or fiber diameters as referred to as draw resonance and an uneven modification degree hardly occur, and spinning is easily carried out.

The central circle 12 does not have to be present; however, it is preferably placed for controlling the cross-section shape of the modified cross-section fiber.

The lower limit of a cool air velocity is preferably not less than 0.5 m/s, more preferably not less than 0.8 m/s, and still more preferably not less than 1.5 m/s. The lower limit of the cool air velocity is within the above-mentioned preferred range, it is easy to fix a fiber shape and variation of a yarn diameter and shape hardly occurs. The upper limit is preferably not more than 20.0 m/s, more preferably not more than 15.0 m/s, and still more preferably not more than 11.0 m/s. The upper limit of the cool air velocity is within the above-mentioned preferred range, deformation of the cross section, for example, agglutination between protrusions within a single yarn in a single fiber cross section hardly occurs.

There are various kinds of applications of the porous fibers in the present invention, and examples of the porous fibers include a filter for various fluids whether gas or liquid phase, a heat insulating material, a sound absorbing material, a shock absorbing material, a substrate for culturing a cell, and a scaffold for regenerative medicine. Particularly, in a medical application, the porous fiber is preferably used for removal of a pathogenic protein, bacteria, virus, endotoxin, sugar chain, autoantibody, immune complex, free light chain, potassium, bilirubin, bile acid, creatinine, phosphorus compound, drug, and the like from blood and blood plasma, and a body fluid. Examples of pathogenic proteins include a cytokine, $\beta_2$-microglobulin ($\beta_2$-MG), a low density lipoprotein, a very low density lipoprotein, and an apolipoprotein. In addition, when the porous fiber is for use in water treatment, it is preferably used for removal of humins, metal corrosions and the like.

Other than a removal of a substance to be adsorbed, a function in which a drug or the like is sustainedly released can be imparted to the fiber by retaining the drug or the like in advance in pores of the porous fiber. As an example of this, when the porous fiber is used for a medical equipment, antithrombogenicity can be enhanced by retaining an anticoagulant agent in advance and, when the porous fiber is used as a substrate for a cell culture, the culture can be controlled by retaining a growth factor or the like.

Besides these, a cell which has phagocytic capacity can be removed by allowing the porous fiber to have a protrusion. Thus, inflammation can be suppressed by actively removing a leukocyte which has phagocytic capacity from blood of e.g., a patient with inflammatory disease. This mechanism is not clear, but it is believed that the cell recognizes a protrusion as a foreign body, whereby it demonstrates phagocytic capacity as it is.

As a spinning method of obtaining the fiber according to the present invention, any of melt spinning and solution spinning can be employed, however, the solution spinning is preferred since, in the solution spinning, a porous fiber having a relatively uniform structure is easily obtained by quickly removing only a solvent from a state in which a support component is uniformly dissolved in the solvent. Therefore, the spinning solution preferably includes a support component such as a resin and a good solvent in which the support component can be dissolved. Although a third component such as fine particles can be mixed as a pore-forming material or a dispersant, there is a possibility that washing efficiency may be reduced or fixation by post-crosslinking may be required depending on use conditions.

When a substance to be adsorbed is the $\beta_2$-MG, the adsorption capacity per fiber volume is preferably not less than 0.005 mg/cm$^3$, more preferably not less than 0.014 mg/cm$^3$, still more preferably not less than 0.020 mg/cm$^3$, and particularly preferably not less than 0.031 mg/cm$^3$. When the adsorption capacity per volume of the porous fiber is within the above-mentioned preferred range, the porous fiber exhibits good adsorption capacity in case that it is packed in a column or the like. Excessively large number of the fibers to be packed is not required in order to secure adsorption capacity, whereby increased column volume is hardly caused and it is possible to suppress the cost and to be handled well. Especially when blood is used as the fluid that is to be treated, a serious adverse effect such as low blood pressure may not be caused because the amount of blood taken out of body is not increased.

The adsorption capacity of the fiber can be easily measured by a batch process by using $\beta_2$-MG, as an adsorption target, which is a pathogenic protein of dialysis-related amyloidosis being complication of long-term dialysis. A method of measuring adsorption capacity is as follows. First, bovine blood to which disodium ethylenediaminetetraacetate is added is adjusted so that hematocrit is 30±3% and total protein level is 6.5±0.5 g/dL. Note that a bovine blood plasma within 5 days after the blood has been drawn is used. Next, $\beta_2$-MG is added so that the concentration is 1 mg/L, and the resulting mixture is stirred. Moreover, the porous fiber is cut into a bundle with length of 8 cm, and the bundle was put, for example, in a 15-mL centrifuge tube manufactured by GREINER Japan Co., so that a volume of the fiber is 0.0905 cm$^3$ and 12 mL of the above-mentioned bovine blood plasma was then added, and the resulting mixture was stirred at room temperature (20° C. to 25° C.) for one hour using a seesaw shaker or the like, for example, Wave-SI manufactured by TAITEC CORPORATION which is set a scale to 38 and an angle to maximum (one turn in 1.7 seconds). In order to measure the $\beta_2$-MG concentration before stirring C1 (mg/mL) and after stirring C2 (mg/mL), each 1 mL is sampled and stored in a freezer of −20° C. or lower. The $\beta_2$-MG concentration was measured by latex agglutination method, and an adsorbed amount per fiber volume and an adsorbed amount per fiber surface area are calculated from the following equations.

Adsorbed amount per fiber volume (mg/cm$^3$)=(C1−C2)×12/0.0905

Adsorbed amount per fiber surface area (mg/cm$^2$)=(C1−C2)×12/(total surface area of fiber cm$^2$)×1,000

The porous fiber according to the present invention can be used as a purification column by being incorporated into a casing having an inlet port and an outlet port for the fluid that is to be treated. Examples of a shape of the casing include polygonal cylinder bodies, such as a square cylinder body and a hexagonal cylinder body and a circular cylindrical body, of which both ends are open ends, and among these, the circular cylindrical body, particularly, a cylinder body with a complete round cross section is preferred. The reason for this is since the casing does not have a corner, retention of blood at a corner can be suppressed. Further, since both sides are open ends, a flow of the fluid that is to be treated hardly becomes turbulent and therefore pressure loss can be minimized. Furthermore, the casing is preferably an instrument composed of plastic, metal or the like. When it is plastic, for example, a thermoplastic resin having excellent mechanical strength and excellent heat stability is used. Specific examples of such thermoplastic resins include polycarbonate-based resins, cellulose-based resins, polyester-based resins, polyarylate-based resins, polyimide-based resins, cyclic polysulfone resins, polyether sulfone resins, polyolefin-based resins, a polystyrene resin, polyvinyl alcohol resins, and mixtures thereof. Among these, polypropylene, polystyrene, polycarbonate and derivatives thereof are preferred from the viewpoint of formability and radiation resistance. Particularly, a resin having excellent transparency such as polystyrene and polycarbonate is advantageous for ensuring safety since an internal state can be recognized in perfusing, for example, blood, and a resin having excellent radiation resistance is preferred in case that radiation is used for sterilization. A resin is manufactured by injection molding with a mold or machining a material. Among these, plastic is preferably used from the viewpoint of cost, formability, weight and blood compatibility.

As a method of sealing an end of the purification column, there are a method of disposing a mesh, and a method in which the end is fixed using a rein, a penetrating hole penetrating through partition walls formed at both ends of casing is provided and thereby the casing inside is communicated with the outside. Here, the penetrating hole refers to an opening which penetrates through partition walls formed at both ends of casing in the lengthwise direction of the porous fiber. That is, the penetrating holes are present on partition walls formed at both ends of casing and penetrates through these, and they are holes through which the casing inside is communicated with the outside. Among these, a method of disposing a mesh is more preferred since a process is easier than a method of forming partition walls formed at both ends of casing and liquid dispersibility into a column is higher. Further, a mesh with a larger pressure loss, a plate, referred to as a baffle or current plate, which controls flow, or the like may be provided for a part of the mesh in order to further enhance dispersibility of the fluid that is to be treated in a column.

A casing length of the purification column is not less than 1 cm and not more than 500 cm, and more preferably not less than 3 cm and not more than 50 cm. When the casing length of the purification column is within the above-mentioned preferred range, insertion of the porous fibers into a column is good and handling in actually using as a purification column is easy. On the other hand, for example, when partition walls are formed at both ends of casing, it is not disadvantageous, for example, handleability after making a column is also good. As used herein, the casing length is a length in an axis direction of a cylindrical casing before partition walls are formed at both ends of casing and caps are fitted.

As a shape of the fibers in incorporating into a column, a straight form is preferred, and it is preferred to insert the fibers of the straight form in parallel to a lengthwise direction of a column case. Since the porous fibers of the straight form easily secure a flow path of the fluid that is to be treated, it is easy to uniformly distribute the fluid that is to be treated in the column. Further, such fibers can suppress resistance of the flow path, and is advantageous to an increase of a pressure loss due to the adhesion of a dissolved substance in the fluid that is to be treated. Therefore, even when highly viscous blood is a fluid that is to be treated, a risk of coagulation in the casing can be kept low. The porous fibers can also be processed as a knit, a fabric or a nonwoven fabric or cut into grains of less than 5 mm. However, since large tension and/or stress is applied to the fiber in processing or shredding, there is such a restriction that a porosity of the fiber cannot be increased. Moreover, the number of process steps is increased by processing the fibers, and the cost is also increased. Further, when the fluid that is to be treated contains a lot of solutes and viscosity is high, it easily results in increased pressure in a column.

The number of fibers with the straight form to be inserted into the column is preferably about 1,000 to 500,000.

In the present invention, the upper limit of a packing ratio of the fiber to a casing is preferably not more than 70%, more preferably 65%, and particularly preferably not more than 62%. The lower limit of a packing ratio is preferably not less than 30%, more preferably not less than 45%, and particularly preferably not less than 52%. When the packing ratio is within the above-mentioned preferred range, insertion of the porous fibers into a casing is good, while the fiber in the casing is hardly one-sided or nonuniform flow in a column hardly occurs.

The packing ratio refers to a ratio between a casing volume (Vc) which is calculated from a cross section area and a length of a casing and a fiber volume (Vf) which is calculated from a fiber cross section area of the fiber, a casing length and the number of the fibers, and it is determined as follows.

$Vc$=Cross section area of casing body×Casing length $Vf$=Cross section area of a fiber×Number of fibers× Casing length Packing ratio=$Vf/Vc$×100(%)

When the casing has a tapered portion, as the cross section area of the casing body, a cross section area at a middle of the casing is used.

Vc as used herein does not include a volume of a member not containing a fiber, for example, a member which serves as outlet/inlet ports for the fluid that is to be treated, such as a member referred to as a header or a header cap. Further, Vf also includes a volume of a spacer fiber or the like which spacer fiber is used for preventing intimate contact between fibers in a case.

An effective length of the fiber refers to a length obtained by subtracting lengths of partition walls formed at both ends of casing from the casing length, and the upper limit of the effective length of the fiber is preferably not more than 5,000 mm, more preferably not more than 500 mm, and particularly preferably not more than 210 mm from the viewpoint that pressure loss increases when fibers are bent or incorporated in a column. The lower limit of the effective length of the fiber is preferably not less than 5 mm, more preferably not less than 20 mm, and particularly preferably not less than 30 mm. When the effective length is within the above-mentioned preferred range, an amount of fibers to be disposed in cutting extra fibers protruding out of a column in order to align the length of fibers, is not increased so much, and thereby resulting in maintaining high productivity and the fiber bundle is easily handled. For measuring the effective length of the fiber, a fiber length is measured in a state of straight form in which both ends of the fiber are stretched in case of a crimped fiber. Specifically, one side of fiber taken out of the column is fixed with a tape or the like and hung vertically, a weight of about 5 g per cross section area ($mm^2$) of the fiber is loaded to the other side and a whole length when the fiber is in a linear form is quickly measured. This measurement is carried out for 30 fibers arbitrarily selected in a column or the like, an average of 30 fibers is calculated in millimeters, and rounded off to unit.

Further, when the fibers are used as a fiber bundle, it is preferred to include a large amount of porous fibers according to the present invention in the bundle from the viewpoint of increasing a surface area per fiber volume, and it is possible to be combined with a fiber having a round cross section. A proportion of the porous fiber according to the present invention in the fiber bundle is not less than 28 vol %, more preferably not less than 36 vol %, still more preferably not less than 45 vol %, and particularly preferably not less than 60 vol %. The fiber bundle thus obtained can be suitably used as an adsorbent material having high adsorption capacity.

The fiber bundle in the present invention may be wrapped by a film, net, mesh, nonwoven fabric, or the like, or one or more fibers may be wrapped in a spiral manner by a finished yarn referred to as a covered yarn in order to prevent poor cohesion by electrostatic repulsion or the like of the porous fibers and to prevent intimate contact between single yarns. Note that the fiber wrapped by such a covered yarn is not included within a multi-filament as described above.

Further, when the column is used as a medical equipment, a technique in which the column is incorporated into an extracorporeal circulation circuit and adsorption/removal are performed online is preferred from the viewpoint of an amount of one throughput or ease of operation. In this case, the purification column according to the present invention may be used singly, or may be used by being connected in series with an artificial kidney in dialysis. By using such a technique concurrently with dialysis, it is possible to remove a substance which only artificial kidney is inadequate to remove. Particularly, a function of the artificial kidney can be complemented by adsorbing/removing a substance having a large molecular weight which is hard to be removed by the artificial kidney using the purification column according to the present invention.

When the purification column is used concurrently with the artificial kidney, it may be connected upstream of the artificial kidney or downstream of the artificial kidney in a circuit. An advantage of connecting upstream of the artificial kidney is that the purification column easily exerts its inherent performance since it is hardly affected by the dialysis by the artificial kidney. On the other hand, an advantage of connecting downstream of the artificial kidney is that concentrations of solutes are high since blood obtained by removing water in the artificial kidney is processed, whereby an increased adsorption/removal efficiency can be expected.

A spinning solution formed by dissolving a polymer in a solvent is prepared. In this, since the radius of pores of the fiber can be larger as the polymer concentration of the spinning solution (concentration of a substance in the spinning solution excluding a solvent) is lower, it is possible to control a radius of pores and a pore amount by appropriately setting the polymer concentration of the spinning solution. In addition to this, it is also possible to control a radius of pores and a pore amount by using a polymer having a negatively charged group. From such a viewpoint, in the present invention, the polymer concentration of the spinning solution is preferably not more than 30% by weight, more preferably not more than 27% by weight, and still more preferably not more than 24% by weight. When the polymer having, for example, methacrylsulfonic acid-p-styrenesulfonic acid as a negatively charged group is used, a proportion of the polymer having methacrylsulfonic acid-p-styrenesulfonic acid which is present in the total polymers is preferably not more than 10 mol %. The fiber is obtained by using a spinneret having, for example, an discharge opening with a modified cross section as shown in FIG. 7 (D=0.20 mm, W=0.10 mm, L=1.0 mm, d=0.25 mm), allowing the spinning solution to pass through the dry air part having a certain distance, and then discharging the spinning solution in a coagulating bath including a poor solvent such as water or a non-solvent. The lower limit of retention time of the fiber in a dry part is as described above and, when a temperature of the discharged fiber is lowered in a dry part to be rapidly structurally fixed such as gelated or coagulated, gelling of the fiber can be promoted by blowing a cool air in the dry part. Further, although a detailed mechanism is not clear, by increasing a cool air velocity to enhance cooling efficiency, it is possible to increase the open pore ratio at the fiber surface and a diameter of the pores adjacent to the periphery of the fiber.

The spinning solution discharged from the spinneret is coagulated in a coagulating bath. The coagulating bath generally includes a mixture with a coagulating agent such as water and/or alcohol, or a solvent constituting the spinning solution. Water is usually used. The radius of pores can be varied by controlling a temperature of the coagulating bath. Since the radius of pores can be affected by the type of the spinning solution or the like, a temperature of the coagulating bath is also appropriately selected. In general, when coagulating bath temperature is elevated, the radius of pores can be enlarged. Although this mechanism is not precisely clear, it is believed that the spinning solution may be coagulated/fixed before the inside of the fiber shrinks since desolvating is fast in a high-temperature bath by a competition reaction of desolvation from the spinning solution and the coagulation/shrinking. For example, a temperature of coagulating bath in case that the fiber contains PMMA is preferably not more than 90° C., more preferably not more than 75° C., and particularly preferably not more than 65° C. When the upper limit of the temperature of coagulating bath is within the above-mentioned preferred range, since the radius of pores is not too large, the porous specific surface area is not decreased, strength/elongation is not decreased, or non-specific adsorption is not increased. The lower limit of the temperature of coagulating bath is preferably not less than 5° C., and more preferably not less than 20° C. When the lower limit of the temperature of coagulating bath is within the above-mentioned preferred range, the radius of pores is not too small and a substance to be adsorbed is easy to be diffused inside the pore.

Then, the fibers are washed in order to remove a solvent adhering to the coagulated fibers. A means for washing the fiber is not particularly limited, but a method of allowing the fiber to pass through a multi-stage bath filled with water (referred to as a water washing bath) is preferably used. A temperature of water in the water washing bath may be determined according to property of a polymer constituting the fiber. For example, in case of the fiber containing PMMA, a temperature of 30° C. to 50° C. is employed.

Further, a process step of providing a moisturizing ingredient for the fibers may be added in order to maintain a radius of pores after water washing bath. The moisturizing ingredient as used herein refers to an ingredient capable of retaining humidity of the fiber, or an ingredient capable of preventing reduction of humidity of the fiber in the air. Typical examples of the moisturizing ingredients include glycerin and an aqueous solution thereof.

After completion of water washing and providing a moisturizing ingredient, in order to enhance dimension stability of the highly shrinkable fiber, the fiber can be allowed to pass through a bath filled with a heated aqueous solution of the moisturizing ingredient (referred to as a heat treatment bath). The heat treatment bath is filled with a heated aqueous solution of the moisturizing ingredient, and the fiber experiences thermal action to shrink by passing through the heat treatment bath, and therefore hardly shrink in the subsequent steps, whereby the fiber structure can be stabilized. A heat treatment temperature in this case varies depending on a fiber material and is preferably not less than 50° C., and more preferably not less than 80° C. in case of a fiber containing PMMA. Further, the heat treatment temperature is preferably not more than 95° C., and more preferably not more than 87° C., which is set.

EXAMPLES

The porous fibers according to the present invention and the purification column incorporating the porous fibers will be described below by means of specific examples.

Example 1

[Preparation of Porous Fibers]

With 376 parts by mass of dimethyl sulfoxide, 31.7 parts by mass of syndiotactic PMMA (hereinafter referred to as syn-PMM) having a mass average molecular weight of 400,000, 31.7 parts by mass of syndiotactic PMMA having a mass average molecular weight of 1,400,000, 16.7 parts by mass of isotactic PMMA (hereinafter referred to as iso-PMM) having a mass average molecular weight of 500,000, and 20 parts by mass of PMMA copolymer having a molecular weight of 300,000 containing 1.5 mol % of sodium p-styrenesulfonate were mixed, and the resulting mixture was stirred at 110° C. for 8 hours to prepare a spinning solution. The viscosity at 92° C. of obtained spinning solution was 1,880 poise. The obtained spinning solution was discharged at a rate of 1.1 g/min from a spinneret which was maintained at 92° C. and had a shape shown in FIG. 6 and an discharge opening with a dimension shown in Table 1 into the air, and the discharged spinning solution was allowed to travel 380 mm through the air part, and then guided to a coagulating bath and allowed to pass through the bath to obtain a solid fiber. Water was used for the coagulating bath and a water temperature (coagulating bath temperature) was 43° C. Each fiber was washed with water, then guided to a bath tank including an aqueous solution containing 70% by weight of glycerin as a moisturizing agent, and then allowed to pass through a heat treatment bath at a temperature of 84° C. to remove extra glycerin, followed by winding at a rate of 16 m/min.

With respect to the obtained fibers, the modification degree Do/Di of the fiber cross section, protrusion width ω, the protrusion shape index ω/Di, the inscribed circle occupancy, the circle equivalent diameter T2, the average radius of pores, the pore radius distribution index, the pore shape index, the open pore ratio at surface, the thickness of the dense layer adjacent to the surface T1, the tensile strength at break, the tensile elongation at break and the adsorption capacity per surface area/per volume were measured in the above-mentioned manner. The results are shown in Tables 1 and 2.

Example 2

Fibers were prepared under the same conditions as in Example 1 except that a spinneret having a shape shown in FIG. 7 and a discharge opening with dimensions shown in Table 1 were used. The results are shown in Tables 1 and 2.

Example 3

Fibers were prepared under the same conditions as in Example 1 except that a spinneret having a shape shown in FIG. 8 and a discharge opening with dimensions shown in Table 1 were used. The results are shown in Tables 1 and 2.

Example 4

Fibers were prepared under the same conditions as in Example 1 except that a spinneret having a shape shown in FIG. 9 and a discharge opening with dimensions shown in Table 1 were used. The results are shown in Tables 1 and 2.

Example 5

Fibers were prepared under the same conditions as in Example 1 except that a spinneret having a shape shown in FIG. 10 and a discharge opening with dimensions shown in Table 1 were used. The results are shown in Tables 1 and 2.

Example 6

Fibers were prepared under the same conditions as in Example 1 except that a spinneret having a shape shown in FIG. 11 and a discharge opening with dimensions shown in Table 1 were used. The results are shown in Tables 1 and 2.

Example 7

Fibers were prepared under the same conditions as in Example 1 except that a spinneret having a shape shown in FIG. 12 and a discharge opening with dimensions shown in Table 1 were used. The results are shown in Tables 1 and 2.

Comparative Example 1

Fibers having a round cross section were prepared under the same conditions as in Example 1 except that a spinneret having a circular discharge opening having φ0.3 was used. The results are shown in Tables 1 and 2.

TABLE 1

| | Shape & Size of Spinneret | | | | | | | | |
|---|---|---|---|---|---|---|---|---|---|
| | Shape of Spinneret (FIG. No.) | D (mm) | W (mm) | L (mm) | L/W | d (mm) | Extrusion Rate g/min | Retention Time at Dry Zone sec | Cooling Air Speed m/s | Coagulation Bath Temperature °C. |
| Example 1 | FIG. 6 | 0.11 | 0.09 | 0.9 | 10.0 | 0.11 | 1.1 | 1.425 | 2.5 | 43 |
| Example 2 | FIG. 7 | 0.11 | 0.09 | 0.9 | 10.0 | 0.11 | 1.1 | 1.425 | 2.5 | 43 |
| Example 3 | FIG. 8 | 0.11 | 0.09 | 0.9 | 10.0 | 0.11 | 1.1 | 1.425 | 2.5 | 43 |
| Example 4 | FIG. 9 | 0.20 | 0.10 | 1.0 | 10.0 | 0.25 | 1.1 | 1.425 | 2.5 | 43 |
| Example 5 | FIG. 10 | 0.20 | 0.10 | 1.0 | 10.0 | 0.25 | 1.1 | 1.425 | 2.5 | 43 |
| Example 6 | FIG. 11 | 0.20 | 0.10 | 1.0 | 10.0 | 0.25 | 1.1 | 1.425 | 2.5 | 43 |
| Example 7 | FIG. 12 | 0.20 | 0.10 | 1.0 | 10.0 | 0.25 | 1.1 | 1.425 | 2.5 | 43 |
| Comparative Example 1 | φ0.3 Circle | — | — | — | — | — | 1.1 | 1.425 | 2.5 | 43 |

| | Winding Speed m/min | Protrusion Number (Protrusion Shape) | Modification Degree Do/Di — | Protrusion Width ω μm | Protrusion Shape Index ω/Di — | Inscribed Circle Occupancy — |
|---|---|---|---|---|---|---|
| Example 1 | 16 | 2 (Ellipse Shape) | 2.40 | 90 | 0.90 | 0.66 |
| Example 2 | 16 | 2 (L Shape) | 2.31 | 89 | 0.90 | 0.63 |
| Example 3 | 16 | 2 (Shape shown in FIG. 8) | 2.33 | 89 | 0.88 | 0.64 |
| Example 4 | 16 | 3 (Y shape) | 2.36 | 48 | 0.54 | 0.59 |
| Example 5 | 16 | 4 (Cross Shape) | 2.13 | 36 | 0.43 | 0.51 |
| Example 6 | 16 | 5 (Star Shape) | 1.51 | 32 | 0.39 | 0.45 |
| Example 7 | 16 | 6 (* Shape) | 1.53 | 28 | 0.36 | 0.40 |
| Comparative Example 1 | 16 | absent (Circle Shape) | 1.00 | — | — | 1.00 |

TABLE 2

| | Equivalent Circle Diameter of Fiber Cross-section T2 μm | Average Radius of Pores nm | Pore Radius Distribution Index — | Porous Specific Surface Area m²/g | Index of Pore Shape (Dxy) — | Open Pore Ratio at Surface % | Thickness of Dense Layer Adjacent to Surface T1 μm |
|---|---|---|---|---|---|---|---|
| Example 1 | 140 | 6.5 | 1.17 | (≥250) | 1.1 | 3.7 | 0.93 |
| Example 2 | 140 | 6.7 | 1.19 | (≥250) | 1.1 | 3.7 | 0.93 |

TABLE 2-continued

| | | | | | | | |
|---|---|---|---|---|---|---|---|
| Example 3 | 140 | 6.4 | 1.18 | (≥250) | 1.1 | 3.6 | 0.90 |
| Example 4 | 140 | 6.6 | 1.19 | 311 | 1.0 | 3.8 | 0.71 |
| Example 5 | 140 | 6.3 | 1.16 | (≥250) | 1.0 | 3.8 | 0.76 |
| Example 6 | 140 | 6.5 | 1.18 | (≥250) | 1.1 | 3.6 | 0.79 |
| Example 7 | 140 | 6.5 | 1.17 | (≥250) | 1.2 | 3.5 | 0.81 |
| Comparative Example 1 | 140 | 6.7 | 1.17 | (≥250) | 1.0 | 3.7 | 0.72 |

| | T1/T2 — | Ratio of Average Diameter of Pores in the Area Adjacent to the Outer Surface vs Average Diameter of Pores in the Center Portion Area — | $\beta_2$-MG Adsorption Amount | | Tensile Fracture Strength gf/mm$^2$ | Tensile Fracture Elongation % |
|---|---|---|---|---|---|---|
| | | | per Surface μg/cm$^2$ | per Volume mg/cm$^3$ | | |
| Example 1 | 0.0066 | 1.12 | 0.099 | 0.033 | 1611 | 59 |
| Example 2 | 0.0066 | 1.02 | 0.099 | 0.033 | 1520 | 55 |
| Example 3 | 0.0064 | 1.08 | 0.097 | 0.032 | 1536 | 56 |
| Example 4 | 0.0051 | 1.12 | 0.095 | 0.038 | 2003 | 49 |
| Example 5 | 0.0054 | 1.09 | 0.102 | 0.046 | 2111 | 45 |
| Example 6 | 0.0056 | 1.11 | 0.105 | 0.051 | 2029 | 40 |
| Example 7 | 0.0058 | 1.09 | 0.099 | 0.048 | 1999 | 34 |
| Comparative Example 1 | 0.0051 | 1.10 | 0.096 | 0.027 | 1387 | 115 |

Examples 1 to 7 shows results in case of modified cross-section fiber in which the protrusion number, that is, the fiber cross section shape was modified. The modification degrees of any are not less than 1.20, that is, they have large surface areas per volume, and also the adsorption capacities per volume are high. Comparative Example 1 shows the results of the so-called round fiber having a modification degree of less than 1.20. It is found that in the round fiber, since the surface area per volume is minimum, the adsorbed amount per volume is limited. In addition, the tensile strength at break is also lower compared with Examples 1 to 7. It is understood that this is due to less dense layer per cross section.

Examples 8 to 13 and Comparative Example 2

Fibers were prepared under the same conditions as in Example 1 except that a spinneret having a shape shown in FIG. 6 and a discharge opening with a dimension were used shown in Table 3. The results are shown in Tables 3 and 4.

TABLE 3

| | Shape & Size of Spinneret | | | | | | | | | |
|---|---|---|---|---|---|---|---|---|---|---|
| | Shape of Spinneret (FIG. No.) | D (mm) | W (mm) | L (mm) | L/W | d (mm) | Extrusion Rate g/min | Retention Time at Dry Zone sec | Cooling Air Speed m/s | Coagulation Bath Temperature ° C. |
| Example 8 | FIG. 6 | 0.11 | 0.09 | 0.3 | 3.3 | 0.11 | 1.1 | 1.425 | 2.5 | 43 |
| Example 9 | FIG. 6 | 0.11 | 0.09 | 0.5 | 5.6 | 0.11 | 1.1 | 1.425 | 2.5 | 43 |
| Example 10 | FIG. 6 | 0.11 | 0.09 | 0.7 | 7.8 | 0.11 | 1.1 | 1.425 | 2.5 | 43 |
| Example 1 | FIG. 6 | 0.11 | 0.09 | 0.9 | 10.0 | 0.11 | 1.1 | 1.425 | 2.5 | 43 |
| Example 11 | FIG. 6 | 0.11 | 0.09 | 1.4 | 15.6 | 0.11 | 1.1 | 1.425 | 2.5 | 43 |
| Example 12 | FIG. 6 | 0.11 | 0.09 | 2.2 | 24.4 | 0.11 | 1.1 | 1.425 | 2.5 | 43 |
| Example 13 | FIG. 6 | 0.11 | 0.09 | 3.0 | 33.3 | 0.11 | 1.1 | 1.425 | 2.5 | 43 |
| Comparative Example 2 | FIG. 6 | 0.11 | 0.09 | 4.0 | 44.4 | 0.11 | 1.1 | 1.425 | 2.5 | 43 |

| | Winding Speed m/min | Protrusion Number (Protrusion Shape) | Modification Degree Do/Di — | Protrusion Width ω μm | Protrusion Shape Index ω/Di — | Inscribed Circle Occupancy — |
|---|---|---|---|---|---|---|
| Example 8 | 16 | 2 (Ellipse Shape) | 1.23 | 119 | 0.85 | 0.86 |
| Example 9 | 16 | 2 (Ellipse Shape) | 1.46 | 113 | 0.87 | 0.82 |
| Example 10 | 16 | 2 (Ellipse Shape) | 2.00 | 97 | 0.88 | 0.74 |
| Example 1 | 16 | 2 (Ellipse Shape) | 2.40 | 90 | 0.90 | 0.66 |
| Example 11 | 16 | 2 (Ellipse Shape) | 3.75 | 71 | 0.89 | 0.44 |
| Example 12 | 16 | 2 (Ellipse Shape) | 6.67 | 54 | 0.90 | 0.25 |
| Example 13 | 16 | 2 (Ellipse Shape) | 8.18 | 50 | 0.91 | 0.21 |
| Comparative Example 2 | 16 | 2 (Ellipse Shape) | 9.60 | 46 | 0.92 | 0.16 |

TABLE 4

| | Equivalent Circle Diameter of Fiber Cross-section T2 μm | Average Radius of Pores nm | Pore Radius Distribution Index — | Porous Specific Surface Area m²/g | Index of Pore Shape (Dxy) — | Open Pore Ratio at Surface % | Thickness of Dense Layer Adjacent to Surface T1 μm |
|---|---|---|---|---|---|---|---|
| Example 8 | 140 | 6.6 | 1.18 | (≥250) | 1.0 | 3.9 | 1.09 |
| Example 9 | 140 | 6.5 | 1.17 | (≥250) | 1.1 | 3.9 | 0.96 |
| Example 10 | 140 | 6.7 | 1.20 | (≥250) | 1.2 | 4.2 | 0.80 |
| Example 1 | 140 | 6.5 | 1.19 | (≥250) | 1.1 | 3.7 | 0.93 |
| Example 11 | 140 | 6.5 | 1.18 | (≥250) | 1.2 | 3.3 | 1.01 |
| Example 12 | 140 | 6.3 | 1.17 | (≥250) | 1.1 | 3.2 | 1.10 |
| Example 13 | 140 | 6.7 | 1.20 | (≥250) | 1.1 | 3.1 | 1.29 |
| Comparative Example 2 | 140 | 6.6 | 1.19 | (≥250) | 1.2 | 2.1 | 2.00 |

| | T1/T2 — | Ratio of Average Diameter of Pores in the Area Adjacent to the Outer Surface vs Average Diameter of Pores in the Center Portion Area — | $\beta_2$-MG Adsorption Amount per Surface μg/cm² | $\beta_2$-MG Adsorption Amount per Volume mg/cm³ | Tensile Fracture Strength gf/mm² | Tensile Fracture Elongation % |
|---|---|---|---|---|---|---|
| Example 8 | 0.0078 | 1.10 | 0.093 | 0.027 | 1442 | 93 |
| Example 9 | 0.0068 | 1.01 | 0.098 | 0.029 | 1475 | 81 |
| Example 10 | 0.0057 | 1.04 | 0.101 | 0.032 | 1553 | 68 |
| Example 1 | 0.0066 | 1.08 | 0.099 | 0.033 | 1611 | 59 |
| Example 11 | 0.0072 | 1.08 | 0.096 | 0.036 | 1807 | 38 |
| Example 12 | 0.0079 | 1.10 | 0.095 | 0.044 | 2229 | 18 |
| Example 13 | 0.0092 | 1.13 | 0.085 | 0.044 | 2449 | 12 |
| Comparative Example 2 | 0.0143 | 1.05 | 0.056 | 0.031 | 2655 | 7 |

Examples 8 to 13 are experiments in which the modification degree was varied, and it is found from Tables 3 and 4 that the adsorption capacity per volume is improved as the modification degree increases, but the adsorption capacity has a maximum point and turns downward when the modification degree is a certain value or more. When the modification degree is too high, such as 9.60, as Comparative Example 2, performance per surface area is reduced, and therefore performance per volume is significantly reduced. A reduction of the surface porosity is thought to be the cause of this. Specifically, it is supposed that since the protrusion becomes long, whereby nonuniform cooling occurs during spinning and, in some place, there may be a location without being adequately blown by cool wind. Further, since an inscribed circle occupancy is decreased in association with increasing a modification degree, the tensile strength at break is reduced and yarn breaking often occurs during spinning in the condition of Comparative Example 2. Therefore, the modification degree is preferably not more than 8.50.

Examples 14 to 18

Fibers were prepared under the same conditions as in Example 1 except that a spinneret having a shape shown in FIG. 10 and a discharge opening with a dimension shown in Table 5 were used, and using a coagulating bath temperature shown in Table 5. The results are shown in Tables 5 and 6.

TABLE 5

| | Shape & Size of Spinneret | | | | | | Extrusion Rate g/min | Retention Time at Dry Zone sec | Cooling Air Speed m/s | Coagulation Bath Temperature ° C. |
|---|---|---|---|---|---|---|---|---|---|---|
| | Shape of Spinneret (FIG. No.) | D (mm) | W (mm) | L (mm) | L/W | d (mm) | | | | |
| Example 14 | FIG. 10 | 0.20 | 0.10 | 1.0 | 10.0 | 0.25 | 1.1 | 1.425 | 2.5 | 85 |
| Example 15 | FIG. 10 | 0.20 | 0.10 | 1.0 | 10.0 | 0.25 | 1.1 | 1.425 | 2.5 | 60 |
| Example 5 | FIG. 10 | 0.20 | 0.10 | 1.0 | 10.0 | 0.25 | 1.1 | 1.425 | 2.5 | 43 |
| Example 16 | FIG. 10 | 0.20 | 0.10 | 1.0 | 10.0 | 0.25 | 1.1 | 1.425 | 2.5 | 30 |
| Example 17 | FIG. 10 | 0.20 | 0.10 | 1.0 | 10.0 | 0.25 | 1.1 | 1.425 | 2.5 | 20 |
| Example 18 | FIG. 10 | 0.20 | 0.10 | 1.0 | 10.0 | 0.25 | 1.1 | 1.425 | 2.5 | 10 |

| | Winding Speed m/min | Protrusion Number (Protrusion Shape) | Modification Degree Do/Di — | Protrusion Width ω μm | Protrusion Shape Index ω/Di — | Inscribed Circle Occupancy — |
|---|---|---|---|---|---|---|
| Example 14 | 16 | 4 (Cross Shape) | 1.83 | 48 | 0.43 | 0.55 |
| Example 15 | 16 | 4 (Cross Shape) | 1.95 | 43 | 0.43 | 0.53 |
| Example 5 | 16 | 4 (Cross Shape) | 2.13 | 36 | 0.43 | 0.51 |

TABLE 5-continued

| | | | | | | |
|---|---|---|---|---|---|---|
| Example 16 | 16 | 4 (Cross Shape) | 2.25 | 34 | 0.43 | 0.49 |
| Example 17 | 16 | 4 (Cross Shape) | 2.29 | 33 | 0.43 | 0.49 |
| Example 18 | 16 | 4 (Cross Shape) | 2.83 | 28 | 0.43 | 0.44 |

TABLE 6

| | Equivalent Circle Diameter of Fiber Cross-section T2 μm | Average Radius of Pores nm | Pore Radius Distribution Index — | Porous Specific Surface Area $m^2/g$ | Index of Pore Shape (Dxy) — | Open Pore Ratio at Surface % | Thickness of Dense Layer Adjacent to Surface T1 μm |
|---|---|---|---|---|---|---|---|
| Example 14 | 150 | 11.4 | 1.97 | 127 | 1.0 | 3.7 | 0.81 |
| Example 15 | 150 | 8.9 | 1.36 | 226 | 1.1 | 3.7 | 0.79 |
| Example 5 | 140 | 6.7 | 1.19 | 307 | 1.0 | 3.8 | 0.76 |
| Example 16 | 132 | 5.1 | 1.17 | 354 | 1.1 | 3.8 | 0.78 |
| Example 17 | 123 | 3.2 | 1.08 | 429 | 1.0 | 3.6 | 0.75 |
| Example 18 | 109 | 0.8 | 1.05 | 505 | 1.1 | 3.5 | 0.75 |

| | T1/T2 — | Ratio of Average Diameter of Pores in the Area Adjacent to the Outer Surface vs Average Diameter of Pores in the Center Portion Area — | $\beta_2$-MG Adsorption Amount | | Tensile Fracture Strength $gf/mm^2$ | Tensile Fracture Elongation % |
|---|---|---|---|---|---|---|
| | | | per Surface μg/cm² | per Volume mg/cm³ | | |
| Example 14 | 0.0054 | 1.09 | 0.089 | 0.034 | 1988 | 50 |
| Example 15 | 0.0053 | 1.00 | 0.099 | 0.038 | 2044 | 48 |
| Example 5 | 0.0054 | 1.07 | 0.102 | 0.046 | 2111 | 45 |
| Example 16 | 0.0059 | 1.11 | 0.101 | 0.050 | 2167 | 43 |
| Example 17 | 0.0061 | 1.04 | 0.100 | 0.054 | 2203 | 42 |
| Example 18 | 0.0069 | 1.09 | 0.059 | 0.041 | 2295 | 41 |

Examples 5 and 14 to 18 show the results when the temperature of coagulating bath was varied and the average radius of pores, the pore radius distribution index, and the porous specific surface area were varied. It is found that the adsorption capacity is also improved as the porous specific surface area is increased. However, in Example 18 in which the average radius of pores is 0.8 nm, the adsorbed amounts per surface area and per volume are slightly reduced. It is thought that the reason for this is that the radius of pores was too small compared to a size of $\beta_2$-MG. Note that porous specific surface areas in Examples 1 to 3, 5 to 13, 19, and 20 were not measured, but these can be estimated to be 250 $m^2/g$ or more since the coagulating bath temperature is 43° C. in any case.

Example 19

[Preparation of Column]

The porous fiber obtained in Example 5 were bundled and incorporated into a polycarbonate cylindrical casing having an inner diameter of 56 mm and an axial length of 58 mm in a straight form so that a packing ratio of the fiber is 53%. Next, polypropylene mesh filters which were cut to a size having a diameter equal to a casing inner diameter and have an opening of an equivalent circle diameter of 84 μm and an aperture ratio of 36%, were fitted to the inlet/outlet of the fluid that is to be treated at both end surfaces of the column. Finally, caps referred to as a header which have the inlet or the outlet of the fluid that is to be treated, were attached to casing ends.

[Measurement of Adsorption Capacity of Column]

As an evaluation of the adsorption capacity of a column, a clearance of $\beta_2$-MG was measured. It is known that $\beta_2$-MG is a pathogenic protein of dialysis-related amyloidosis which is a complication of long-term dialysis.

Blood plasma was obtained from bovine blood to which disodium ethylenediaminetetraacetate is added by centrifugal separation. The blood plasma was adjusted so that hematocrit is 30±3% and an amount of total protein is 6.5±0.5 g/dL. Note that a bovine blood plasma within 5 days after the blood has been drawn is used. Next, bovine blood plasma $\beta_2$-MG is added so that the concentration is 1 mg/L, and the resulting mixture is stirred. Such bovine blood plasma was separated into 2 L for circulation and 1.5 L for clearance measurement.

A circuit was set as in FIG. 13. In the circuit, an inlet part from which the fluid that is to be treated was taken in was designated as Bi, and a fluid outlet part after the fluid passed through the purification column was designated as Bo.

Bi was placed in a beaker for circulation in which 2 L of the bovine blood plasma (37° C.) adjusted above and the pump was then allowed to start at a flow rate of 200 mL/min, and Bo was placed into a beaker for circulation to bring the fluid into circulation immediately after a portion for 90 seconds of fluid discharged from Bo was disposed.

After the fluid was circulated for 1 hour, the pump was stopped.

Next, Bi was placed in the bovine blood plasma for clearance measurement adjusted above, and Bo was placed in the beaker for disposal. A flow rate was set to 200 mL/min, and 10 mL of a sample was taken from the bovine blood plasma (37° C.) for clearance measurement after a lapse of two minutes from the start of the pump and designated as Bi fluid. After a lapse of four minutes 30 seconds from the start of the pump, 10 mL of a sample flown from Bo was taken and designated as Bo fluid. These samples were stored in a freezer at −20° C. or lower.

A clearance was calculated by the following Formula I from a $\beta_2$-MG concentration of each fluid. Since there may be a case that a measured value is different from the other depending on a lot of the bovine blood, the same lot of the bovine blood plasma was used for all Examples and Comparative Examples.

$$Co\ (mL/min)=(CBi-CBo)\times Q_B/CBi \qquad (I)$$

In Formula I, Co=$\beta_2$-MG clearance (mL/min), CBi=b$\beta_2$-MG concentration in Bi fluid, CBo=$\beta_2$-MG concentration in Bo fluid, $Q_B$=Bi pump flow rate (mL/min). The results are shown in Table 7.

Example 20

A column was made in the same way as in Example 19 except that the fiber obtained in Example 11, and adsorption capacity of the column was measured. The results are shown in Table 7.

Comparative Example 3

A column was made in the same way as in Example 19 except that the fiber obtained in Comparative Example 1, and adsorption capacity of the column was measured. The results are shown in Table 7.

TABLE 7

|  | Adsorption Performance of Column mL/min |
| --- | --- |
| Example 19 | 68 |
| Example 20 | 57 |
| Comparative Example 3 | 49 |

From the results of measuring adsorption capacity of columns in Examples 19 and 20 and Comparative Example 3, the surface area per fiber volume is increased by modifying the cross section of the fiber, and therefore adsorption capacity is improved.

Example 21

A column was produced by the same way as in Example 19. After the column was washed with 10 L of RO water, an aqueous solution containing 1,000 ppm of ethanol as an antioxidant was packed therein, and irradiated with gamma ray with an exposure dose of 25 kGy. Thereafter, the fiber was removed by disassembling the column, the number of adhered platelets was evaluated. The results are shown in Table 8.

[Measurement of the Numbers of Adhered Platelets in Contact with Human Blood]

After blood was sampled from a healthy adult, heparin sodium injection (manufactured by AY Pharmaceuticals Co., Ltd.) was immediately added as an anticoagulant agent so that it was 100 U/mL. Said blood was brought into contact with the fiber which was removed by disassembling the column within 30 minutes after sampling the blood, and shaken at 37° C. for 2 hours. Thereafter, the fiber was washed with saline, blood components were fixed with 2.5 vol % glutaraldehyde (manufactured by Nacalai Tesque Inc.) saline solution, followed by washing with distilled water. Said fiber was pasted on a sample stage for a microscope and dried under reduced pressure at 0.1 torr or less at room temperature for 10 hours. Subsequently, a platinum/palladium thin layer was formed by sputtering on a surface of a hollow fiber membrane, this was used as a sample, and the sample surface which was an inner surface of the hollow fiber membrane was observed at a magnification of 1,500 times using a field emission-typed scanning electron microscope (S-800, manufactured by Hitachi High-Technologies Corp.), and the numbers of adhered platelets in one visual field ($4.3\times10^3$ μm$^2$) was counted. This was repeated for 50 portions of the fiber surface, and the average was determined.

Example 22

A column was made in the same way as in Example 21 except that an aqueous solution containing 500 ppm of ethanol as an antioxidant was filled to the column, and the number of adhered platelets was evaluated. The results are shown in Table 8.

Example 23

A column was made in the same way as in Example 21 except that an aqueous solution containing 200 ppm of ethanol as an antioxidant was filled to the column, and the number of adhered platelets was evaluated. The results are shown in Table 8.

Example 24

A column was made in the same way as in Example 21 except that an aqueous solution containing 100 ppm of ethanol as an antioxidant was filled to the column, and the number of adhered platelets was evaluated. The results are shown in Table 8.

Example 25

A column was made in the same way as in Example 21 except that an aqueous solution containing 1,000 ppm of butanol as an antioxidant was filled to the column, and the number of adhered platelets was evaluated. The results are shown in Table 8.

Example 26

A column was made in the same way as in Example 21 except that an aqueous solution containing 1,000 ppm of hexanol as an antioxidant was filled to the column, and the number of adhered platelets was evaluated. The results are shown in Table 8.

Example 27

A column was made in the same way as in Example 21 except that an aqueous solution containing 1,000 ppm of heptanol as an antioxidant was filled to the column, and the number of adhered platelets was evaluated. The results are shown in Table 8.

Example 28

A column was made in the same way as in Example 19 except that the fiber obtained in Example 2 was used, washed with 10 L of RO water, filled with an aqueous solution containing 1,000 ppm of ethanol as an antioxidant, and irradiated with gamma ray with an exposure dose of 25 kGy. Thereafter, the fiber was removed by disassembling the column, the number of adhered platelets was evaluated. The results are shown in Table 8.

Comparative Example 4

A column was made in the same way as in Comparative Example 3. After the column was washed with 10 L of RO water, and irradiated with gamma ray with an exposure dose of 25 kGy. Thereafter, the fiber was removed by disassembling the column, the number of adhered platelets was evaluated. The results are shown in Table 8.

Comparative Example 5

A column was produced by the same way as in Example 19. After the column was washed with 10 L of RO water, and irradiated with gamma ray with an exposure dose of 25 kGy. Thereafter, the fiber was removed by disassembling the column, the number of adhered platelets was evaluated. The results are shown in Table 8.

TABLE 8

|  | Number of Adhered Platalets pieces/(4.3 × 10³ μm²) |
| --- | --- |
| Example 21 | 3 |
| Example 22 | 7 |
| Example 23 | 14 |
| Example 24 | 21 |
| Example 25 | 3 |
| Example 26 | 3 |
| Example 27 | 3 |
| Example 28 | 7 |
| Comparative Example 4 | 19 |
| Comparative Example 5 | 32 |

From Comparative Examples 4 and 5, it is shown that the number of adhered platelets of the oval-shaped yarn is more than that of the round-shaped yarn. From the results of Examples 21 to 27, it is shown that the number of adhered platelets is largely decrease by irradiating gamma ray in the presence of an antioxidant even in case of the oval-shaped yarn. From the results of Examples 21 and 28, it is shown that the number of adhered platelets of L-shaped yarn is slightly more than that of the oval-shaped yarn. This is because a platelet is easy to be adhered to a crevice portion in an L-shaped yarn.

DESCRIPTION OF REFERENCE SIGNS

1: Circumscribed circle
2: Inscribed circle
3: Diameter of a circumscribed circle Do
4: Diameter of an inscribed circle Di
5: Concentric circle passing points which divides a line segment of radius into five parts with an equal length
6: Central portion area
7: Adjacent area to the outer surface
8: Center of an inscribed circle
9: Tip portion of a protrusion,
10: Point at which a straight line connecting between a center of an inscribed circle and a tip portion of a protrusion and the inscribed circle intersect.
11: Protrusion width ω
12: Central circle portion
13: Width of a slit W
14: Length of a slit L
15: Tip circle portion
16: Purification column
17: Pump
18: Hot water bath at 37° C.
19: Beaker for disposal
20: Blood plasma for circulation
21: Blood plasma for clearance measurement There are various kinds of applications of the porous fibers according to the present invention, and application examples of the porous fibers include a filter for various fluids whether gas or liquid phase, a heat insulating material, a sound absorbing material, a shock absorbing material, a substrate for culturing a cell, and a scaffold for regenerative medicine. Particularly, in medical application, the porous fibers are suitably used for removal of pathogenic proteins from blood and blood plasma, or body fluid.

The invention claimed is:

1. A porous fiber having pores inside the fiber and comprising a modified solid cross-section, wherein the porous fiber satisfies the following (a) and (b):
   (a) a modification degree Do/Di in the modified solid cross-section is 1.20 to 8.50 where an inscribed circle diameter of the modified solid cross-section is denoted by Di and a circumscribed circle diameter of the modified solid cross-section is denoted by Do; and
   (b) a porous specific surface area of the fiber is not less than 170 m²/g.

2. The porous fiber according to claim 1, wherein an inscribed circle occupancy of the following equation is not less than 0.10:

Inscribed circle occupancy=Area of the inscribed circle of a cross section of the fiber/Area of the cross section of the fiber.

3. The porous fiber according to claim 1, wherein a diameter of the pores in the porous fiber is not more than 25 μm and a ratio of an average diameter of the pores in the area adjacent to the outer surface of the fiber versus an average diameter of the pores in the central portion area of the fiber is not less than 0.50 and not more than 3.00.

4. The porous fiber according to claim 1, wherein the modified solid cross-section comprises a porous portion which has a network structure composed of a communication hole and a dense layer which has a more dense structure in comparison to the porous portion, and wherein the porous fiber satisfies the following (d) to (f):
   (d) the porous fiber has a continuous structure of the porous portion and the dense layer;
   (e) the dense layer is located closer to the area adjacent to the outer surface of the fiber than the porous portion and a distance T1 from the outermost surface of the fiber to the porous portion is not less than 0.001 μm and not more than 30 μm; and
   (f) the network structure satisfies a pore shape index calculated by the following equation that is not less than 0.2 and not more than 6.0:

index of pore shape in a cross section in the fiber axis direction $D_{xy}$=(pore diameter in the lengthwise direction of the fiber)/(pore diameter in the cross-section direction of the fiber).

5. The porous fiber according to claim 4, wherein both the porous portion and the dense layer contain not less than 45 vol % of a material common to both as a component material.

6. The porous fiber according to claim 1, wherein the solid fiber is in a straight form.

7. The porous fiber according to claim 1, wherein an open pore ratio at the surface of the porous fiber is not less than 0.5% and not more than 30%.

8. The porous fiber according to claim 1, wherein the porous fiber has a negative charge.

9. The porous fiber according to claim 1, wherein the porous fiber comprises an amorphous polymer material.

10. The porous fiber according to claim 1, wherein the porous fiber comprises an amorphous polymer material and the amorphous polymer material comprises a polymer with an ester group.

11. The porous fiber according to claim 1, wherein the number of adhered platelets which are brought into contact with the surface of the porous fiber is not more than $30/(4.3 \times 10^3 \ \mu m^2)$.

12. An adsorbent material, comprising not less than 28 vol % of the porous fiber according to claim 1 as a fiber bundle.

13. The adsorbent material according to claim 12, wherein the adsorbent material is for use in a medical application.

14. The adsorbent material according to claim 13, wherein the adsorption amount of $\beta_2$-microglobulin per fiber volume is not less than 0.005 mg/cm$^3$.

15. The porous fiber according to claim 1, wherein the modified solid cross-section comprises a porous portion which has a network structure composed of a communication hole, and a layer, and wherein the porous fiber satisfies the following (d) to (f):
(d) the porous fiber has a continuous structure of the porous portion and the layer;
(e) the layer is located closer to the area adjacent to the outer surface of the fiber than the porous portion and a distance T1 from the outermost surface of the fiber to the porous portion is not less than 0.001 μm and not more than 30 μm; and
(f) the network structure satisfies a pore shape index calculated by the following equation that is not less than 0.2 and not more than 6.0:

index of pore shape in a cross section in the fiber axis direction $Dxy$=(pore diameter in the lengthwise direction of the fiber)/(pore diameter in the cross-section direction of the fiber).

16. The porous fiber according to claim 15, wherein both the porous portion and the layer contain not less than 45 vol % of a material common to both as a component material.

* * * * *